(12) United States Patent
Peri et al.

(10) Patent No.: US 10,342,717 B2
(45) Date of Patent: Jul. 9, 2019

(54) ABSORBENT ARTICLE AND DISTRIBUTION MATERIAL

(71) Applicant: The Procter & Gamble Company, Cincinnati, OH (US)

(72) Inventors: Andrea Peri, Kronberg (DE); Kenneth Michael Hamall, West Chester, OH (US); Aniruddha Chatterjee, Kelkheim (DE); Joerg Endres, Frankfurt am Main (DE); Mattias Schmidt, Idstein (DE); Sandra Sautter, Rosbach V. D. Höhe (DE); Gene Xiaoqing Huang, Mason, OH (US); Darrell Ian Brown, Mason, OH (US); Ward William Ostendorf, West Chester, OH (US); Joseph Leslie Grolmes, Madeira, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 904 days.

(21) Appl. No.: 14/943,044

(22) Filed: Nov. 17, 2015

(65) Prior Publication Data

US 2016/0136012 A1    May 19, 2016

(30) Foreign Application Priority Data

Nov. 18, 2014  (EP) .................................... 14193690

(51) Int. Cl.
*A61F 13/15* (2006.01)
*A61F 13/535* (2006.01)
(Continued)

(52) U.S. Cl.
CPC .......... *A61F 13/535* (2013.01); *A61F 13/537* (2013.01); *A61F 13/5376* (2013.01);
(Continued)

(58) Field of Classification Search
CPC .............. A61F 13/535; A61F 13/53409; A61F 13/537; A61F 13/53713; A61F 13/53717;
(Continued)

(56) References Cited

U.S. PATENT DOCUMENTS 3,700,623 A    10/1972  Keim
3,772,076 A    11/1973  Keim
(Continued)

FOREIGN PATENT DOCUMENTS

EP    0617164 B1    8/1997
EP    1447066 A1    8/2004
(Continued)

OTHER PUBLICATIONS

US 5,972,466 A, 10/1999, Trokhan (withdrawn)
(Continued)

*Primary Examiner* — Jacqueline F Stephens
(74) *Attorney, Agent, or Firm* — Wednesday G. Shipp; Christian M. Best

(57) ABSTRACT

An absorbent article comprises a liquid permeable topsheet, a liquid impermeable backsheet, an absorbent core between the topsheet and the backsheet. The absorbent core comprises an absorbent material. The absorbent article further comprises a distribution material between the topsheet and the absorbent core. The distribution material is notionally divided in a front region, a back region and a middle region located between the front and the back region. Each of the front, back and middle regions is ⅓ of the length of the distribution material. At least one of the front, back and middle regions of the distribution material comprises one or more layers. The one or more layers of the distribution material comprise a fibrous structure made of wet-laid fibers.

19 Claims, 15 Drawing Sheets

(51) Int. Cl.
   *A61F 13/534* (2006.01)
   *A61F 13/537* (2006.01)
   *A61F 13/53* (2006.01)

(52) U.S. Cl.
   CPC .. *A61F 13/53409* (2013.01); *A61F 13/53713* (2013.01); *A61F 13/53717* (2013.01); *A61F 13/53747* (2013.01); *A61F 13/53752* (2013.01); *A61F 2013/530021* (2013.01); *A61F 2013/530036* (2013.01); *A61F 2013/530437* (2013.01); *A61F 2013/53786* (2013.01)

(58) Field of Classification Search
   CPC .......... A61F 13/53747; A61F 13/53752; A61F 13/5376; A61F 2013/530021; A61F 2013/530036; A61F 2013/530437; A61F 2013/53786
   See application file for complete search history.

(56) References Cited

U.S. PATENT DOCUMENTS

| | | | |
|---|---|---|---|
| 3,860,003 | A | 1/1975 | Buell |
| 4,391,878 | A | 7/1983 | Drach |
| 4,557,801 | A | 12/1985 | Avis |
| 4,637,859 | A | 1/1987 | Trokhan |
| 5,151,092 | A | 9/1992 | Buell et al. |
| 5,217,445 | A * | 6/1993 | Young ............... A61F 13/15203 604/378 |
| 5,221,274 | A | 6/1993 | Buell et al. |
| 5,300,054 | A * | 4/1994 | Feist ................. A61F 13/15203 604/358 |
| 5,509,914 | A | 4/1996 | Osborn, III |
| 5,514,523 | A | 5/1996 | Trokhan et al. |
| 5,520,778 | A | 5/1996 | Sawdai |
| 5,527,428 | A | 6/1996 | Trokhan |
| 5,529,664 | A | 6/1996 | Trokhan |
| 5,534,326 | A | 7/1996 | Trokhan |
| 5,549,589 | A * | 8/1996 | Horney ............. A61F 13/53747 604/366 |
| 5,549,790 | A | 8/1996 | Van |
| 5,552,345 | A | 9/1996 | Schrantz |
| 5,554,145 | A | 9/1996 | Roe et al. |
| 5,554,467 | A | 9/1996 | Trokhan |
| 5,556,509 | A | 9/1996 | Trokhan |
| 5,562,645 | A | 10/1996 | Tanzer et al. |
| 5,566,724 | A | 10/1996 | Trokhan |
| 5,569,234 | A | 10/1996 | Buell et al. |
| 5,575,786 | A | 11/1996 | Osborn, III |
| 5,580,411 | A | 12/1996 | Nease et al. |
| 5,580,423 | A | 12/1996 | Ampulski |
| 5,599,335 | A | 2/1997 | Goldman et al. |
| 5,609,725 | A | 3/1997 | Van |
| 5,614,061 | A | 3/1997 | Phan |
| 5,624,790 | A | 4/1997 | Trokhan |
| 5,628,876 | A | 5/1997 | Ayers |
| 5,629,052 | A | 5/1997 | Trokhan |
| 5,637,194 | A | 6/1997 | Ampulski |
| 5,654,076 | A | 8/1997 | Trokhan |
| 5,656,132 | A | 8/1997 | Farrington, Jr. |
| 5,665,082 | A | 9/1997 | Boulanger |
| 5,674,663 | A | 10/1997 | Mcfarland |
| 5,679,222 | A | 10/1997 | Rasch |
| 5,693,187 | A | 12/1997 | Ampulski |
| 5,693,406 | A | 12/1997 | Wegele |
| 5,709,775 | A | 1/1998 | Trokhan |
| 5,714,041 | A | 2/1998 | Ayers |
| 5,716,692 | A | 2/1998 | Warner |
| 5,718,806 | A | 2/1998 | Trokhan |
| 5,728,268 | A | 3/1998 | Weisman |
| 5,741,402 | A | 4/1998 | Trokhan |
| 5,744,007 | A | 4/1998 | Trokhan |
| 5,776,307 | A | 7/1998 | Ampulski |
| 5,776,311 | A | 7/1998 | Trokhan |
| 5,776,312 | A | 7/1998 | Trokhan |
| 5,779,860 | A | 7/1998 | Hollenberg et al. |
| 5,795,440 | A | 8/1998 | Ampulski |
| 5,804,036 | A | 9/1998 | Phan |
| 5,804,281 | A | 9/1998 | Phan |
| 5,814,190 | A | 9/1998 | Van |
| 5,817,377 | A | 10/1998 | Trokhan |
| 5,820,730 | A | 10/1998 | Phan |
| 5,830,558 | A | 11/1998 | Barnholtz |
| 5,832,362 | A | 11/1998 | Trokhan |
| 5,837,103 | A | 11/1998 | Trokhan |
| 5,840,403 | A | 11/1998 | Trokhan |
| 5,840,411 | A | 11/1998 | Stelljes, Jr. |
| 5,843,279 | A | 12/1998 | Phan |
| 5,846,379 | A | 12/1998 | Ampulski |
| 5,855,572 | A | 1/1999 | Schmidt |
| 5,855,738 | A | 1/1999 | Weisman |
| 5,855,739 | A | 1/1999 | Ampulski |
| 5,858,554 | A | 1/1999 | Neal |
| 5,861,082 | A | 1/1999 | Ampulski |
| 5,865,950 | A | 2/1999 | Vinson |
| 5,871,887 | A | 2/1999 | Trokhan |
| 5,885,421 | A | 3/1999 | Ensign |
| 5,893,965 | A | 4/1999 | Trokhan |
| 5,895,623 | A | 4/1999 | Trokhan et al. |
| 5,897,745 | A | 4/1999 | Ampulski |
| 5,900,122 | A | 5/1999 | Huston |
| 5,904,811 | A | 5/1999 | Ampulski |
| 5,906,710 | A | 5/1999 | Trokhan |
| 5,906,711 | A | 5/1999 | Barnholtz |
| 5,919,556 | A | 7/1999 | Barnholtz |
| 5,935,381 | A | 8/1999 | Trokhan |
| 5,938,893 | A | 8/1999 | Trokhan |
| 5,942,085 | A | 8/1999 | Neal |
| 5,948,210 | A | 9/1999 | Huston |
| 5,951,537 | A | 9/1999 | Osborn, III |
| 5,954,097 | A | 9/1999 | Boutilier |
| 5,962,860 | A | 10/1999 | Trokhan |
| 5,972,813 | A | 10/1999 | Polat |
| 5,980,691 | A | 11/1999 | Weisman |
| 6,004,306 | A | 12/1999 | Robles et al. |
| 6,010,598 | A | 1/2000 | Boutilier |
| 6,030,690 | A | 2/2000 | Mcneil |
| 6,039,839 | A | 3/2000 | Trokhan |
| 6,048,938 | A | 4/2000 | Neal |
| 6,074,525 | A | 6/2000 | Richards |
| 6,086,715 | A | 7/2000 | Mcneil |
| 6,090,241 | A | 7/2000 | Trokhan |
| 6,099,781 | A | 8/2000 | Ampulski |
| 6,103,062 | A | 8/2000 | Ampulski |
| 6,103,067 | A | 8/2000 | Stelljes, Jr. |
| 6,103,953 | A | 8/2000 | Cree et al. |
| 6,106,670 | A | 8/2000 | Weisman |
| 6,110,324 | A | 8/2000 | Trokhan |
| 6,113,723 | A | 9/2000 | Mcneil |
| 6,117,270 | A | 9/2000 | Trokhan |
| 6,117,525 | A | 9/2000 | Trokhan |
| 6,136,146 | A | 10/2000 | Phan |
| 6,139,686 | A | 10/2000 | Trokhan |
| 6,149,849 | A | 11/2000 | Ampulski |
| 6,165,319 | A | 12/2000 | Heath |
| 6,171,447 | B1 | 1/2001 | Trokhan |
| 6,187,138 | B1 | 2/2001 | Neal |
| 6,193,839 | B1 | 2/2001 | Ampulski |
| 6,193,847 | B1 | 2/2001 | Trokhan |
| 6,200,419 | B1 | 3/2001 | Phan |
| 6,210,644 | B1 | 4/2001 | Trokhan |
| 6,238,682 | B1 | 5/2001 | Klofta |
| 6,251,331 | B1 | 6/2001 | Ampulski |
| 6,258,516 | B1 | 7/2001 | Trokhan |
| 6,271,532 | B1 | 8/2001 | Trokhan |
| 6,273,996 | B1 | 8/2001 | Hollenberg et al. |
| 6,287,425 | B1 | 9/2001 | Richards |
| 6,287,641 | B1 | 9/2001 | Ostendorf |
| 6,296,862 | B1 | 10/2001 | Paul |
| 6,329,565 | B1 | 12/2001 | Dutkiewicz |
| 6,344,241 | B1 | 2/2002 | Ampulski |
| 6,358,030 | B1 | 3/2002 | Ampulski |

(56) References Cited

U.S. PATENT DOCUMENTS

| | | |
|---|---|---|
| 6,358,594 B1 | 3/2002 | Ampulski |
| 6,368,465 B1 | 4/2002 | Stelljes, Jr. |
| 6,420,013 B1 | 7/2002 | Vinson |
| 6,420,100 B1 | 7/2002 | Trokhan |
| 6,423,186 B1 | 7/2002 | Trokhan |
| 6,432,272 B1 | 8/2002 | Hollenberg et al. |
| 6,458,447 B1 | 10/2002 | Cabell |
| 6,464,831 B1 | 10/2002 | Trokhan |
| 6,500,307 B2 | 12/2002 | Richards |
| 6,540,880 B1 | 4/2003 | Trokhan |
| 6,551,453 B2 | 4/2003 | Weisman |
| 6,554,601 B2 | 4/2003 | Ampulski |
| 6,561,781 B1 | 5/2003 | Ampulski |
| 6,576,090 B1 | 6/2003 | Trokhan |
| 6,576,091 B1 | 6/2003 | Cabell |
| 6,590,136 B1 | 7/2003 | Young |
| 6,660,129 B1 | 12/2003 | Cabell |
| 6,673,202 B2 | 1/2004 | Burazin |
| 6,706,152 B2 | 3/2004 | Burazin |
| 6,733,833 B2 | 5/2004 | Ampulski |
| 6,743,571 B1 | 6/2004 | Hill |
| 6,746,570 B2 | 6/2004 | Burazin |
| 6,746,766 B2 | 6/2004 | Bond |
| 6,749,719 B2 | 6/2004 | Burazin |
| 6,787,000 B2 | 9/2004 | Burazin |
| 6,790,314 B2 | 9/2004 | Burazin |
| 6,797,114 B2 | 9/2004 | Hu |
| 6,802,937 B2 | 10/2004 | Johnston |
| 6,808,790 B2 | 10/2004 | Chen et al. |
| 6,821,385 B2 | 11/2004 | Burazin |
| 6,821,386 B2 | 11/2004 | Weisman |
| 6,860,970 B2 | 3/2005 | Ampulski |
| 6,890,872 B2 | 5/2005 | Bond |
| 6,913,859 B2 | 7/2005 | Hill |
| 6,946,506 B2 | 9/2005 | Bond |
| 7,094,320 B1 | 8/2006 | Phan |
| 7,118,647 B2 | 10/2006 | Cabell |
| 7,128,809 B2 | 10/2006 | Vinson |
| 7,265,067 B1 | 9/2007 | Phan |
| 7,311,800 B2 | 12/2007 | Russell |
| 7,374,638 B2 | 5/2008 | Horenziak |
| 7,374,639 B2 | 5/2008 | Ampulski |
| 7,419,569 B2 | 9/2008 | Hermans |
| 7,494,563 B2 | 2/2009 | Edwards |
| RE40,724 E | 6/2009 | Barnholtz |
| 7,687,140 B2 | 3/2010 | Manifold |
| 7,691,229 B2 | 4/2010 | Vinson |
| 7,704,601 B2 | 4/2010 | Manifold |
| 7,741,234 B2 | 6/2010 | Smith |
| 7,744,576 B2 | 6/2010 | Busam et al. |
| 7,744,723 B2 | 6/2010 | Sheehan |
| 7,750,203 B2 | 7/2010 | Becker et al. |
| 7,799,411 B2 | 9/2010 | Ostendorf |
| 7,807,022 B2 | 10/2010 | Hermans |
| 7,811,665 B2 | 10/2010 | Manifold |
| 7,851,667 B2 | 12/2010 | Becker |
| 7,869,964 B2 | 1/2011 | Rosati |
| 7,894,625 B2 | 2/2011 | Tompkins, IV |
| 7,914,649 B2 | 3/2011 | Ostendorf |
| 7,922,705 B2 | 4/2011 | Ampulski |
| 7,939,168 B2 | 5/2011 | Manifold |
| 8,025,966 B2 | 9/2011 | Manifold |
| 8,034,463 B2 | 10/2011 | Leimbach et al. |
| RE42,968 E | 11/2011 | Sheehan |
| 8,135,170 B2 | 3/2012 | Tompkins, IV |
| 8,163,130 B2 | 4/2012 | Polat |
| 8,178,196 B2 | 5/2012 | Manifold |
| 8,192,836 B2 | 6/2012 | Manifold |
| 8,202,605 B2 | 6/2012 | Ostendorf |
| 8,211,271 B2 | 7/2012 | Polat |
| 8,282,783 B2 | 10/2012 | Phan |
| 8,287,693 B2 | 10/2012 | Phan |
| 8,298,376 B2 | 10/2012 | Polat |
| 8,313,617 B2 | 11/2012 | Polat |
| 8,657,997 B2 | 2/2014 | Polat et al. |
| 9,439,815 B2 | 9/2016 | Marinelli |
| 2002/0123728 A1 | 9/2002 | Graef et al. |
| 2002/0168518 A1 | 11/2002 | Bond |
| 2003/0077444 A1 | 4/2003 | Bond |
| 2003/0092343 A1 | 5/2003 | Bond |
| 2003/0138597 A1 | 7/2003 | Ruthven |
| 2003/0168912 A1 | 9/2003 | Wodrich |
| 2003/0171729 A1 | 9/2003 | Kaun et al. |
| 2003/0181115 A1 | 9/2003 | Nagasuna |
| 2004/0009387 A1 | 1/2004 | Aoki |
| 2004/0023003 A1 | 2/2004 | Basler |
| 2004/0025887 A1 | 2/2004 | Scopton |
| 2004/0112783 A1 | 6/2004 | Mukai |
| 2004/0154767 A1 | 8/2004 | Trokhan |
| 2004/0154768 A1 | 8/2004 | Trokhan |
| 2004/0154769 A1 | 8/2004 | Lorenz |
| 2004/0157524 A1 | 8/2004 | Polat |
| 2004/0162536 A1 | 8/2004 | Becker et al. |
| 2004/0167486 A1 | 8/2004 | Busam |
| 2004/0192136 A1 | 9/2004 | Gusky |
| 2004/0261639 A1 | 12/2004 | Vaughn |
| 2005/0026529 A1 | 2/2005 | Bond |
| 2005/0034828 A1 | 2/2005 | Graff |
| 2005/0045293 A1 | 3/2005 | Hermans |
| 2005/0067126 A1 | 3/2005 | Horenziak |
| 2005/0079785 A1 | 4/2005 | Bond |
| 2005/0178513 A1 | 8/2005 | Russell |
| 2005/0201965 A1 | 9/2005 | Kuhlman |
| 2005/0215967 A1 | 9/2005 | Toro |
| 2006/0137840 A1 | 6/2006 | Burazin |
| 2007/0156108 A1 | 7/2007 | Becker |
| 2007/0167928 A1 | 7/2007 | Becker |
| 2007/0179464 A1 | 8/2007 | Becker |
| 2007/0232178 A1 | 10/2007 | Polat |
| 2007/0250026 A1 | 10/2007 | Venturino et al. |
| 2007/0254550 A1 | 11/2007 | Hamed et al. |
| 2007/0256802 A1 | 11/2007 | Sheehan |
| 2008/0041543 A1 | 2/2008 | Dyer |
| 2008/0125735 A1 | 5/2008 | Busam |
| 2008/0260996 A1 | 10/2008 | Heilman |
| 2008/0312622 A1 | 12/2008 | Hundorf et al. |
| 2009/0043273 A1 | 2/2009 | Carlucci |
| 2009/0099793 A1 | 4/2009 | Rosati |
| 2009/0110998 A1 | 4/2009 | Miyachi |
| 2009/0118689 A1 | 5/2009 | Lawson et al. |
| 2009/0220741 A1 | 9/2009 | Manifold |
| 2009/0220769 A1 | 9/2009 | Manifold |
| 2009/0287174 A1 | 11/2009 | Carlucci |
| 2010/0036342 A1 | 2/2010 | Carlucci |
| 2010/0051166 A1 | 3/2010 | Hundorf et al. |
| 2010/0228210 A1 | 9/2010 | Busam |
| 2010/0228211 A1 | 9/2010 | Becker |
| 2010/0239946 A1 | 9/2010 | Miyachi |
| 2010/0294446 A1 | 11/2010 | Manifold |
| 2011/0027563 A1 | 2/2011 | Manifold |
| 2011/0114277 A1 | 5/2011 | Spitzer |
| 2011/0125119 A1 | 5/2011 | Weismantel |
| 2011/0137624 A1 | 6/2011 | Weisman et al. |
| 2011/0139389 A1 | 6/2011 | Phan |
| 2011/0139390 A1 | 6/2011 | Phan |
| 2011/0183132 A1 | 7/2011 | Manifold |
| 2011/0189435 A1 | 8/2011 | Manifold |
| 2011/0189436 A1 | 8/2011 | Manifold |
| 2011/0189442 A1 | 8/2011 | Manifold |
| 2011/0189443 A1 | 8/2011 | Manifold |
| 2011/0189451 A1 | 8/2011 | Manifold |
| 2011/0206913 A1 | 8/2011 | Manifold |
| 2011/0207837 A1 | 8/2011 | Luckert |
| 2011/0212299 A1 | 9/2011 | Nyangiro |
| 2011/0250413 A1 | 10/2011 | Lu et al. |
| 2011/0253329 A1 | 10/2011 | Manifold |
| 2011/0268932 A1 | 11/2011 | Catalan et al. |
| 2011/0305884 A1 | 12/2011 | Manifold |
| 2011/0319848 A1 | 12/2011 | McKiernan et al. |
| 2012/0107568 A1 | 5/2012 | Manifold |
| 2012/0277709 A1 | 11/2012 | Marinelli |
| 2013/0018348 A1 | 1/2013 | Carlucci et al. |
| 2013/0167305 A1 | 7/2013 | Weisman |
| 2013/0172226 A1 | 7/2013 | Dreher et al. |

(56) References Cited

U.S. PATENT DOCUMENTS

| | | |
|---|---|---|
| 2013/0209749 A1 | 8/2013 | Myangiro et al. |
| 2013/0226120 A1* | 8/2013 | Van De Maele ... A61F 13/5323 604/372 |
| 2014/0005625 A1 | 1/2014 | Wirtz et al. |
| 2014/0053994 A1 | 2/2014 | Manifold et al. |
| 2014/0163503 A1 | 6/2014 | Arizti et al. |
| 2014/0163511 A1 | 6/2014 | Roe et al. |
| 2016/0074249 A1 | 3/2016 | Rosati et al. |
| 2016/0136009 A1 | 5/2016 | Weisman et al. |
| 2016/0136011 A1 | 5/2016 | Peri et al. |
| 2016/0136013 A1 | 5/2016 | Peri |
| 2017/0258647 A1 | 9/2017 | Orr |
| 2018/0001879 A1 | 1/2018 | Witte |

FOREIGN PATENT DOCUMENTS

| | | |
|---|---|---|
| EP | 1505207 A2 | 2/2005 |
| EP | 0677612 B2 | 6/2006 |
| EP | 187629 A2 | 1/2008 |
| EP | 2740449 | 6/2014 |
| EP | 2740452 | 6/2014 |
| GB | 2319539 A | 5/1998 |
| GB | 2510665 | 8/2014 |
| JP | 2002506888 | 3/2002 |
| WO | WO95/11652 | 5/1995 |
| WO | WO9511652 | 5/1995 |
| WO | WO9633310 A1 | 10/1996 |
| WO | WO9717494 A1 | 5/1997 |
| WO | WO9718783 | 5/1997 |
| WO | WO9844194 A1 | 10/1998 |
| WO | WO 0246510 | 6/2002 |
| WO | WO2005021868 A1 | 3/2005 |
| WO | WO2005068720 A1 | 7/2005 |
| WO | WO2005080683 A2 | 9/2005 |
| WO | WO2006060814 A2 | 6/2006 |
| WO | WO2007001576 A1 | 1/2007 |
| WO | WO2007070124 A1 | 6/2007 |
| WO | WO2012/052172 | 4/2012 |

OTHER PUBLICATIONS

International Search Report, PCT/US2015/060969, dated Feb. 8, 2016, 12 pages.

El-Hosseiny, et al., "Effect of Fiber Length and Coarseness of the Burst Strength of Paper", TAPPI Journal, vol. 82: No. 1 (Jan. 1999), pp. 202-203.

Smook, Gary A., Second Edition Handbook for Pulp & Paper Technologists, 1992, Angus Wilde Publications, Chapter 13, pp. 194-208.

All Office Actions, Responses, Claims for U.S. Appl. No. 14/543,967, dated Nov. 18, 2014.

All Office Actions, Responses, Claims for U.S. Appl. No. 14/543,973, dated Nov. 18, 2014.

All Office Actions, Responses, Claims for U.S. Appl. No. 14/543,984, dated Nov. 18, 2014.

* cited by examiner

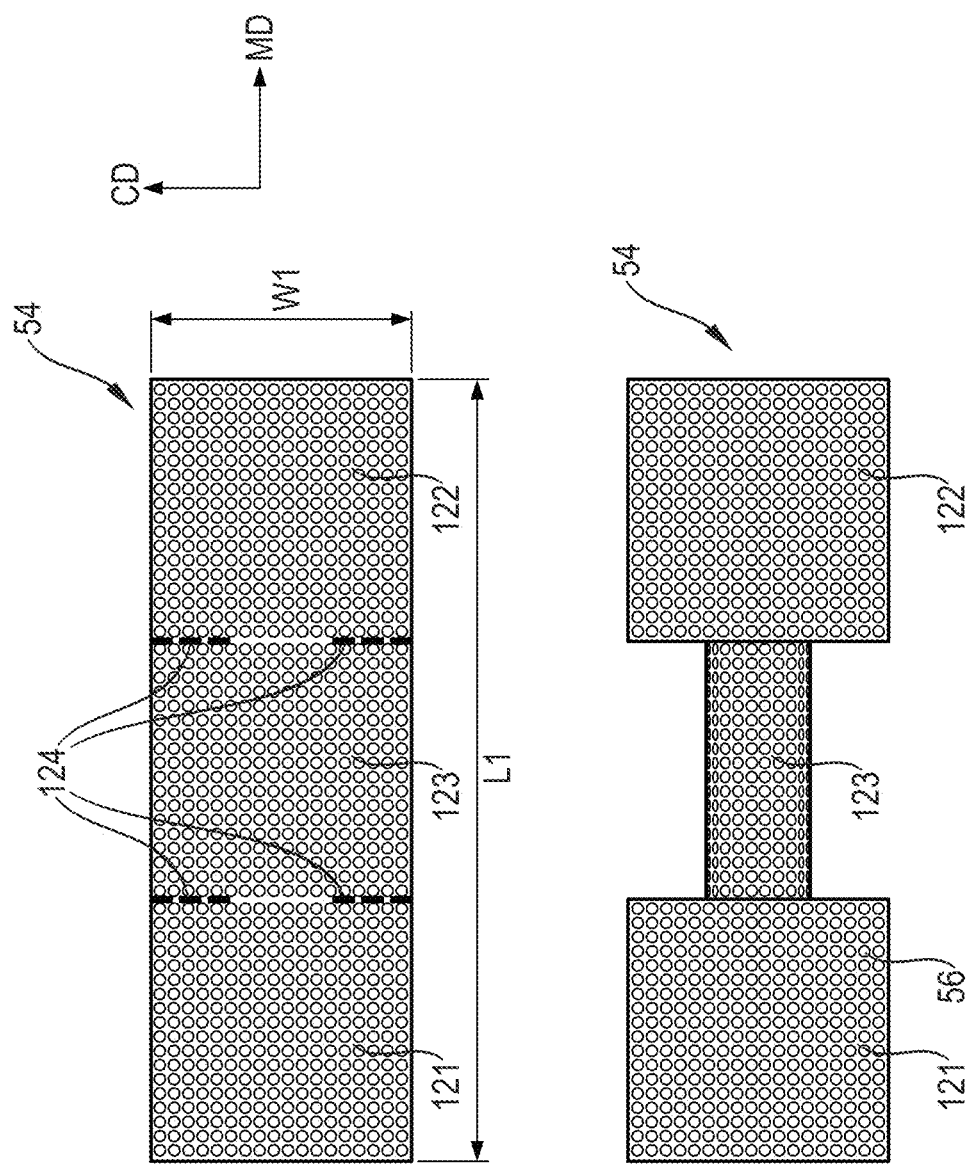

ABSORBENT ARTICLE AND DISTRIBUTION MATERIAL

FIELD OF THE INVENTION

The invention provides an absorbent article for personal hygiene such as a baby diaper, a training pant, a feminine hygiene sanitary napkin or an adult incontinence product. The absorbent article comprises a distribution material.

BACKGROUND OF THE INVENTION

An absorbent article typically comprises a topsheet, a backsheet, and an absorbent core disposed between the topsheet and the backsheet. Optionally, the absorbent core can further include an acquisition layer and a distribution material. The distribution material is able to receive the liquid bodily exudates and distribute and transfer them to the absorbent core in order to render the absorbent core more efficient. The distribution material is typically made of fibers such as synthetic fibers, modified or unmodified cellulosic fibers, or combinations thereof.

When the distribution material is made of unconsolidated air-laid fibers, the distribution material might be adversely affected especially in the wet state during use. Indeed, cracks and disruptions in the structure of an air-laid distribution material can occur. Due to the disruptions, the distribution material might not be able to fully provide the desired distributive properties any more.

There is thus a desire to develop a distribution material for an absorbent article which has an improved wet integrity in its overall structure.

The majority of currently marketed absorbent articles comprise an absorbent core with absorbent material in a form of a blend of cellulosic fibers (so called "airfelt") with superabsorbent polymers in particulate form, see for example U.S. Pat. No. 5,151,092 (Buell). Absorbent articles having an absorbent core consisting essentially of superabsorbent polymers as absorbent material (so called "airfelt-free" cores) have also been proposed, see for example WO 2012/052172 (Van Malderen). In the case of an absorbent article comprising an "airfelt-free" core, the bulk of the absorbent article may be mainly due to the caliper of the distribution material made of air-laid fibers.

There is a desire to develop a distribution material, especially for absorbent articles having an "airfelt-free" core, which has a reduced bulk especially in the dry state. The distribution material may be made of a material which is available at low cost.

SUMMARY OF THE INVENTION

An absorbent article for personal hygiene is provided and comprises a liquid permeable topsheet, a liquid impermeable backsheet, and an absorbent core between the topsheet and the backsheet. The absorbent core comprises an absorbent material. The absorbent article further comprises a distribution material between the topsheet and the absorbent core. The distribution material is notionally divided in a front region, a back region and a middle region located between the front and the back region. Each of the front, back and middle regions is ⅓ of the length of the distribution material. At least one of the front, back and middle regions of the distribution material comprises one or more layers. The one or more layers of the distribution material comprise a fibrous structure made of wet-laid fibers. The one or more layers of the distribution material exhibit a Wet Burst Strength from 50 to 500 g according to the Wet Burst Strength Test Method. The one or more layers of the distribution material have a dry caliper at a pressure of 2.06 kPa from 0.1 mm to 1.0 mm and the one or more layers of the distribution material have a total dry caliper at a pressure of 2.06 kPa from 1.0 mm to 30.0 mm according to Dry Caliper measurement Test Method.

The absorbent article for personal hygiene may comprise a liquid permeable topsheet, a liquid impermeable backsheet, and an absorbent core between the topsheet and the backsheet. The absorbent article may further comprise a distribution material between the topsheet and the absorbent core. The distribution material may be notionally divided in a front region, a back region and a middle region located between the front and the back region. Each of the front, back and middle regions may be ⅓ of the length of the distribution material. At least in the middle region of the distribution material, the distribution material may have from 2 to 10 layers or from 2 to 5 layers. Each layer of the distribution material may comprise a fibrous structure made of wet-laid fibers. Each layer may exhibit a basis weight from 10 to 200 gsm or from 10 to 60 gsm and a Wet Burst Strength from 50 to 500 g according to the Wet Burst Strength Test Method. The middle region of the distribution material may have an overall basis weight from 50 to 250 gsm. Each layer may comprise a pattern of raised elements. Each layer may have a dry caliper at a pressure of 2.06 kPa from 0.5 mm to 1.0 mm and the middle region of the distribution material may have a total dry caliper at a pressure of 2.06 kPa from 1.0 mm to 30.0 mm according to the Dry Caliper measurement Test Method.

Nowhere in the distribution material, the total dry caliper at a pressure of 2.06 kPa may be less than 1.0 mm and nowhere in the distribution material, the total dry caliper at a pressure of 2.06 kPa may be more than 30.0 mm.

The distribution material may not comprise air-laid fibers.

The absorbent material may be encapsulated in one or more substrates, wherein the substrate facing the topsheet may be made of a nonwoven web.

The raised elements of the pattern of raised elements may protrude from each layer of the distribution material towards the topsheet or the raised elements of the pattern of raised elements may protrude from each layer of the distribution material towards the absorbent core.

The raised elements of the pattern of raised elements may protrude from a first group of one or more layers of the distribution material towards the topsheet and the raised elements of the pattern of raised elements may protrude from a second group of one or more layers of the distribution material towards the absorbent core.

The pattern of raised elements may be a random pattern, a pattern or a non-random pattern.

Each raised element may have a shape selected from the group consisting of circles, ellipses, squares, rectangles and combinations thereof.

The first and second pattern of adhesive may comprise a plurality of adhesive lines which may be generally parallel to a longitudinal axis of the absorbent article or which may be generally parallel to a transverse axis of the absorbent article.

The distribution material may comprise one sheet of fibrous structure. The distribution material may comprise a first, second and central subsections wherein the central subsection may be folded to form from 2 to 10 layers.

The first and second subsections of the distribution material may remain unfolded.

The central subsection may coincide with the middle region of the distribution material.

The central subsection may be larger than the middle region along the longitudinal axis of the distribution material 54.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

FIG. 12A is a top view of a sheet of the fibrous structure;

FIG. 12B is a top view of an exemplary distribution material in a "dog bone" shape according to the present invention.

DETAILED DESCRIPTION OF THE INVENTION

Definition of Terms

Figure 1:
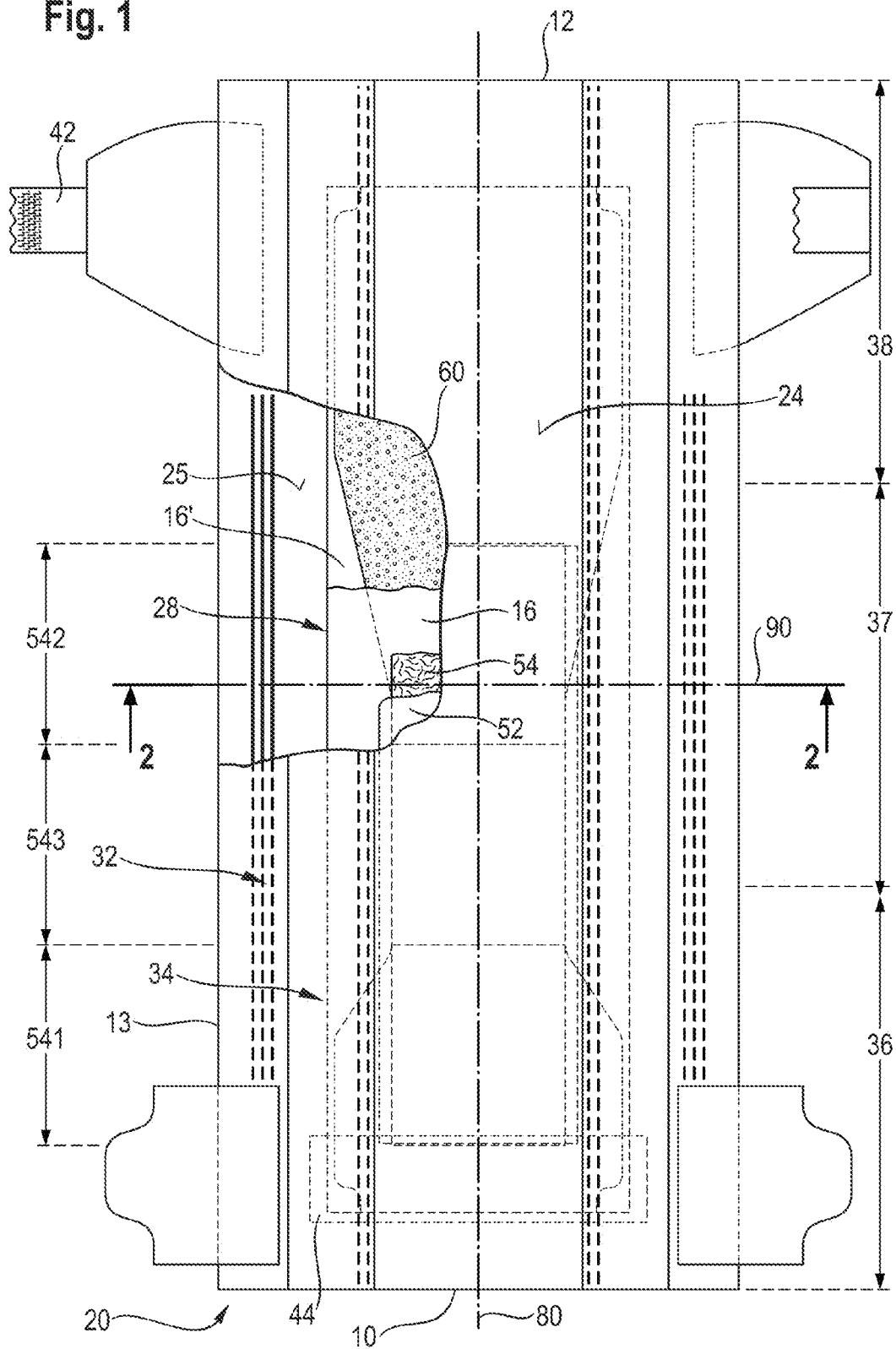
FIG. 1 is a top view of an absorbent article in the form of a diaper comprising an exemplary absorbent core according to the invention with some layers partially removed.

The term "absorbent article" as used herein refers to disposable products such as diapers, training pants or feminine hygiene sanitary napkins and the like which are placed against or in proximity to the body of the wearer to absorb and contain the various liquid bodily exudates discharged from the body. Typically these absorbent articles comprise a topsheet, backsheet, an absorbent core and optionally an acquisition layer and/or distribution material and typically other components, with the absorbent core normally placed between the backsheet and the acquisition system or topsheet. The absorbent article of the present invention may be a diaper or pant.

The term "absorbent core" as used herein refers to a component, which is placed or is intended to be placed within an absorbent article and which comprises an absorbent material enclosed in a core wrap. The term "absorbent core" does not include an acquisition or distribution material or any other component of an absorbent article which is not either an integral part of the core wrap or placed within the core wrap. The absorbent core is typically the component of an absorbent article which comprises all, or at least the majority of, superabsorbent polymer and has the highest absorbent capacity of all the components of the absorbent article.

The term "diaper" as used herein refers to an absorbent article that is intended to be worn by a wearer about the lower torso to absorb and contain liquid bodily exudates discharged from the body. Diapers may be worn by infants (e.g. babies or toddlers) or adults. They may be provided with fastening elements.

The term "pant" as used herein refers to an absorbent article having fixed edges, a waist opening and leg openings designed for infant or adult wearers. A pant-type absorbent article is placed in position on the wearer by inserting the wearer's legs into the leg openings and sliding the pant-type absorbent article into position about the wearer's lower torso. A pant may be preformed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened).

The term "substantially free of absorbent material" or "substantially absorbent material free" as used herein means that the basis weight of the absorbent material in the substantially absorbent material free areas is at least less than 10%, in particular less than 5%, or less than 2%, of the basis weight of the absorbent material in the rest of the absorbent core.

"Comprise," "comprising," and "comprises" are open ended terms, each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essential of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "advantageously" and the likes also qualify features which are not intended to limit the scope of the claims unless specifically indicated to do so.

The term "wet-laid fiber" as used herein comprises cellulosic fibers which have been suspended in an aqueous medium, such as water, before being converted into a web according to a wet-laid papermaking process.

The term "cellulosic fiber" as used herein refers to natural fibers which typically are wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web.

The term "sheet of fibrous structure" as used herein means an individual, integral fibrous structure. Each sheet of fibrous structure may be folded to form from 2 to 10 layers. The term "caliper" as used herein means the thickness of a product sample under a defined load, e.g. at 2.06 kPa.

The term "air-laid fiber" as used herein means fibers which have been provided in a fluid medium which is gaseous (air).

General Description of the Absorbent Article 20

Figure 3:
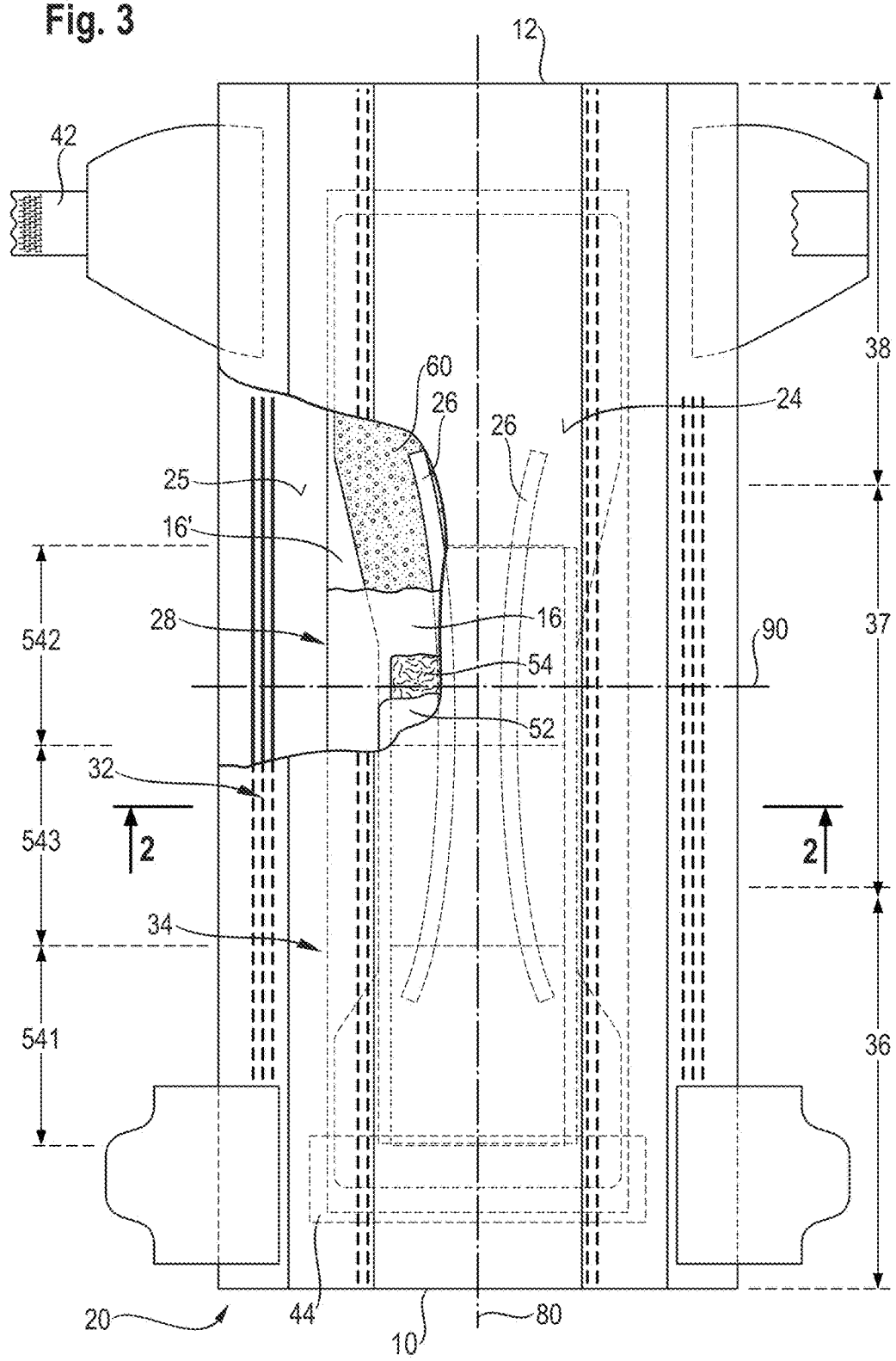
FIG. 3 is a top view of an absorbent article in the form of a diaper comprising another exemplary construction of an absorbent core according to the invention with some layers partially removed.

An exemplary absorbent article 20 in which the absorbent core 28 of the invention can be used is a taped diaper 20 as represented in FIG. 1; and in FIG. 3 with a different absorbent core construction. FIG. 1 and FIG. 3 are top plan views of the exemplary diaper 20, in a flat-out state, with portions of the structure being cut-away to more clearly show the construction of the diaper 20. This diaper 20 is shown for illustration purpose only as the invention may be used for making a wide variety of diapers or other absorbent articles.

The absorbent article 20 comprises a liquid permeable topsheet 24, a liquid impermeable backsheet 25, an absorbent core 28 between the topsheet 24 and the backsheet 25. The absorbent article 20 comprises a front edge 10, a back edge 12, and two longitudinal side edges 13. The front edge 10 is the edge of the absorbent article 20 which is intended to be placed towards the front of the user when worn, and the back edge 12 is the opposite edge. The absorbent article 20 may be notionally divided by a longitudinal axis 80 extending from the front edge to the back edge of the absorbent article 20 and dividing the absorbent article 20 in two substantially symmetrical halves relative to this axis, when viewing the absorbent article 20 from the wearer facing side in a flat out configuration, as exemplarily shown in FIG. 1 and FIG. 3.

Figure 2:
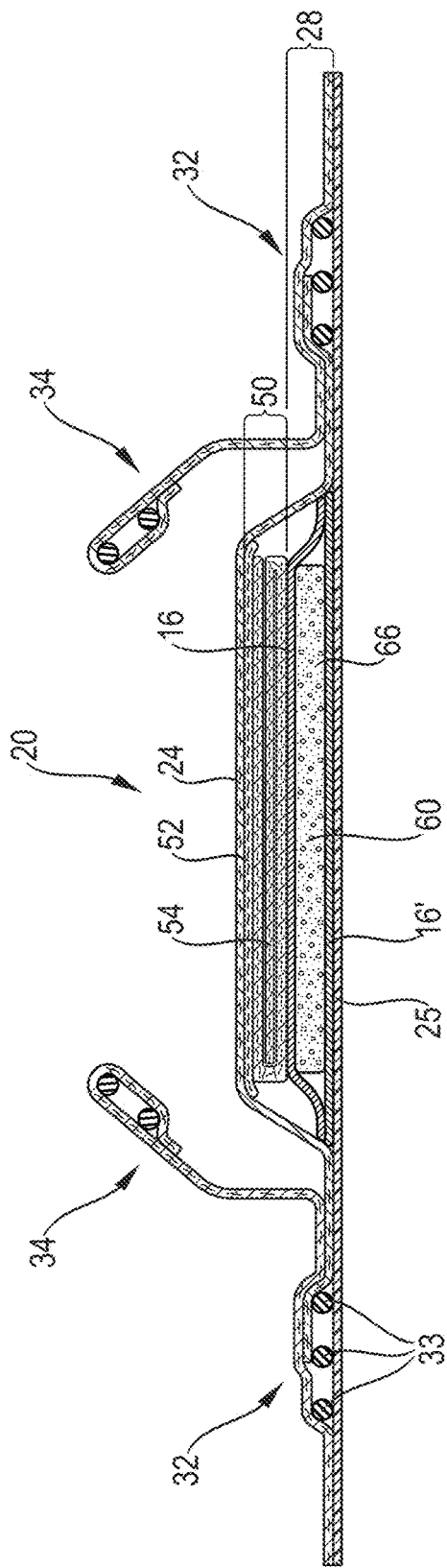
FIG. 2 is a transversal cross-section of the diaper of FIG. 1.

The absorbent article 20 comprises a distribution material 54 and may further comprise an acquisition layer 52 which may be placed on top of the distribution material 54 (the acquisition and distribution material are collectively referred to as acquisition-distribution system "ADS", designated as 50 in FIG. 2), and elasticized gasketing cuffs 32 present between the topsheet 24 and the backsheet 25 and upstanding barrier leg cuffs 34. FIGS. 1-2 and 3-4 also show other typical taped diaper components such as a fastening system comprising fastening tabs 42 attached towards the back edge 12 of the absorbent article 20 and cooperating with a landing zone 44 towards the front edge 10 of the absorbent article 20. The absorbent article 20 may also comprise other typical components, which are not represented in the Figures, such as a back elastic waist feature, a front elastic waist feature, transverse barrier cuff(s), a lotion application, etc.

The absorbent article 20 can also be notionally divided by a transversal axis 90 in a front region and a back region of equal length measured on the longitudinal axis, when the absorbent article 20 is in such a flat state. The absorbent article's transversal axis 90 is perpendicular to the longitudinal axis 80 and placed at half the length of the absorbent article 20. The length of the absorbent article 20 can be measured along the longitudinal axis 80 from the front edge 10 to the back edge 12 of the absorbent article 20.

The absorbent article 20 is notionally divided in a front region 36, a back region 38 and a crotch region 37 located between the front and the back region of the absorbent article 20. Each of the front, back and crotch regions is ⅓ of the length of the absorbent article 20.

The topsheet 24, the backsheet 25, the absorbent core 28 and the other absorbent article components may be assembled in a variety of well known configurations, in particular by adhesive bonding and/or heat and/or pressure embossing. Exemplary diaper assemblies are for example generally described in U.S. Pat. Nos. 3,860,003, 5,221,274, 5,554,145, 5,569,234, 5,580,411, and 6,004,306.

The absorbent core 28 of the present invention may comprise as absorbent material 60 a blend of cellulosic fibers (so called "airfelt") with superabsorbent polymers in particulate form encapsulated in one or more substrates, see for example U.S. Pat. No. 5,151,092 (Buell). Alternatively, the absorbent core 28 may be airfelt free as described in detail below.

Some components of the absorbent article 20 will now be discussed in more details.

"Airfelt-free" Absorbent Core 28

The absorbent core 28 of the invention may comprise an absorbent material 60 with a high amount of superabsorbent polymers (SAP) enclosed within a core wrap. The absorbent material 60 may comprise from 80% to 100% of SAP, such as SAP particles, by weight of the absorbent material 60. The core wrap is not considered as an absorbent material 60 for the purpose of assessing the percentage of SAP in the absorbent core 28.

By "absorbent material" it is meant a material which has at least some absorbency and/or liquid retaining properties, such as SAP, cellulosic fibers as well as some hydrophilically treated synthetic fibers. Typically, adhesives used in making absorbent cores have no absorbency properties and are not considered as absorbent material. The SAP content may be higher than 80%, for example at least 85%, at least 90%, at least 95% and even up to and including 100% of the weight of the absorbent material 60 contained within the core wrap. This high SAP content may provide a relatively thin absorbent core 28 compared to conventional absorbent cores typically comprising between 40-60% SAP and 40-60% of cellulosic fibers. The absorbent material 60 of the invention may in particular comprise less than 10% weight percent, or less than 5% weight percent, or even be substantially free of natural and/or synthetic fibers. The absorbent material 60 may advantageously comprise little or no cellulosic fibers, in particular the absorbent core 28 may comprise less than 15%, 10%, or 5% (airfelt) cellulosic fibers by weight of the absorbent core 28, or even be substantially free of cellulose fibers. Such absorbent core 28 may be relatively thin and thinner than conventional airfelt cores. FIG. 1 and FIG. 2 are illustrations of an absorbent article 20 comprising an "airfelt-free" absorbent core 28.

"Airfelt-free" absorbent cores 28 comprising relatively high amount of SAP with various absorbent core designs have been proposed in the past, see for example in U.S. Pat. No. 5,599,335 (Goldman), EP1447066A1 (Busam), WO95/11652 (Tanzer), US2008/0312622A1 (Hundorf), and WO2012/052172 (Van Malderen).

The absorbent core 28 of the invention may further comprise adhesive for example to help immobilizing the SAP within the core wrap and/or to ensure integrity of the core wrap, in particular when the core wrap is made of one or more substrates. The core wrap will typically extend over a larger area than strictly needed for containing the absorbent material 60 within.

Core Wrap

The absorbent material 60 is encapsulated in one or more substrates.

The core wrap comprises the top side 16 facing the topsheet 24 and the bottom side 16' facing the backsheet 25. The core wrap may be made of a single substrate folded around the absorbent material 60. The core wrap may be made of two substrates (one mainly providing the top side 16 and the other mainly providing the bottom side 16') which are attached to another, as exemplarily shown in FIG. 2. Typical configurations are the so-called C-wrap and/or sandwich wrap. In a C-wrap, as exemplarily shown in FIG. 4, the longitudinal and/or transversal edges of one of the substrate are folded over the other substrate to form flaps. These flaps are then bonded to the external surface of the other substrate, typically by bonding with an adhesive.

The core wrap may be formed by any materials suitable for receiving and containing the absorbent material 60. Typical substrate materials used in the production of conventional absorbent cores may be used, in particular fibrous structures made of wet-laid fibers, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range from 5 gsm to 15 gsm. Suitable materials are for example disclosed in U.S. Pat. No. 7,744,576, US2011/0268932A1, US2011/0319848A1 or US2011/0250413A1. Nonwoven materials provided from synthetic fibers may be used, such as PE, PET and in particular PP.

When the core wrap is made of two (or more) substrates, the two (or more) substrates of the core wrap may be made of the same type of material, or may be made of different materials or one of the substrate may be treated differently than the other to provide it with different properties. In the present invention, at least the substrate facing the topsheet 24 is made of a nonwoven web.

The top side 16 of the core wrap may be sealed to the bottom side 16' of the core wrap at least partially along all the edges of the absorbent core 28. The term "seal" is to be understood in a broad sense. The seal does not need to be continuous along the whole periphery of the core wrap but may be discontinuous along part or the whole of it, such as formed by a series of closely spaced apart seal points on a line. Typically a seal may be formed by adhesive bonding and/or thermal bonding.

Figure 4:
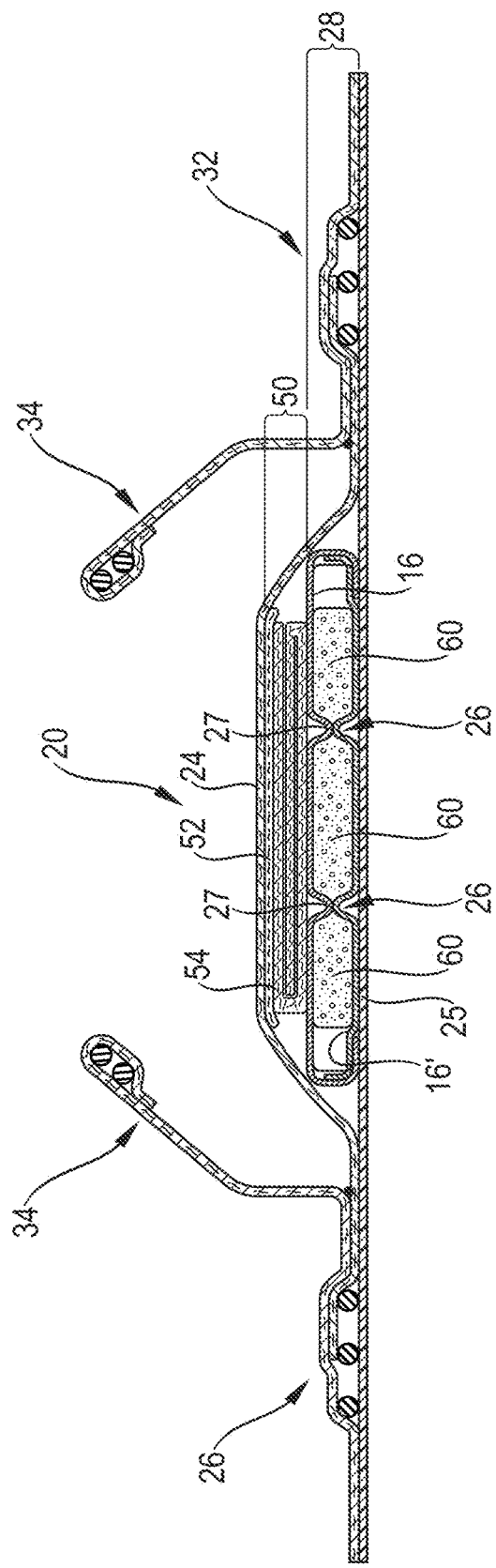
FIG. 4 is a transversal cross-section of the diaper of FIG. 3.

When the core wrap is formed by two substrates, one seal per edge of the absorbent core 28 may typically be used to enclose the absorbent material 60 within the core wrap. As shown in FIG. 4, for example, a first substrate including the top side 16 of the core wrap may be placed on one side of the absorbent core 28 and extends around the absorbent core's longitudinal edges to at least partially wrap an opposed bottom side of the absorbent core 28. A second substrate including the bottom side 16' of the core wrap can be present between the wrapped flaps of the first substrate of the core wrap and the absorbent material 60 of the absorbent core 28. The flaps of the first substrate of the core wrap may be adhesively bonded to the second substrate of the core wrap to provide a seal. This so called C-wrap construction can provide benefits such as improved resistance to bursting in a wet loaded state compared to a sandwich seal. A front edge and back edge of the core wrap may then also be sealed for example by bonding the first substrate and second substrate of the core wrap, flat to another to provide more complete enclosure of the absorbent material 60 across the whole of the periphery of the absorbent core 28. In the so-called sandwich construction, the first and second substrates of the core wrap may also extend outwardly on all edges of the absorbent core 28 and be sealed flat along the whole or parts of the periphery of the absorbent core 28 typically by adhesive bonding and/or heat/pressure bonding. Alternatively, the core wrap may also be formed by a single substrate which may enclose as in a parcel wrap the absorbent material 60.

"Airfelt-free" Absorbent Core 28 Comprising Substantially Absorbent Material Free Areas 26

The absorbent core 28 may comprise an absorbent material deposition area defined by the periphery of the layer formed by the absorbent material 60 within the core wrap.

The absorbent core 28 comprises one or more substantially absorbent material free area(s) 26 which is/are substantially free of absorbent material 60 and through which a portion of the top side 16 of the core wrap is attached by one or more core wrap bond(s) 27 to a portion of the bottom side 16' of the core wrap. In particular, there can be no absorbent material 60 in these areas. Minimal amount such as contaminations with absorbent material 60 that may occur during the making process are not considered as absorbent material 60. The one or more substantially absorbent material free area(s) 26 is/are advantageously confined by the absorbent material 60, which means that the substantially absorbent material free area(s) 26 do(es) not extend to any of the edge of the absorbent material deposition area.

If the substantially absorbent material free area 26 extends to any of the edges of the absorbent material deposition area, each substantially absorbent material free area 26 may have areas of absorbent material 60 on either side of each substantially absorbent material free area 26.

The portions of the top side 16 and the bottom side 16' of the core wrap may be attached together continuously along the substantially absorbent material free area(s) 26. However, one or more core wrap bonds 27 along the substantially absorbent material free area(s) 26 may also be discontinuous (intermittent) such as series of point bonds. The core wrap bond(s) (27) may be provided by known attachment means, such as adhesive bonding, pressure bonding, ultrasonic bonding or heat bonding, dynamic mechanical bonding or combination thereof.

The attachment of the portions of the top side 16 and the bottom side 16' of the core wrap may be provided by one or more adhesives, in particular one or more layers of adhesive and/or one or more layers of fibrous adhesive material, if present in the absorbent core 28. These adhesives may therefore serve the dual function of immobilizing the absorbent material 60 and attach the top side 16 to the bottom side 16' of the core wrap together at one or more substantially absorbent material free area(s) 26.

The absorbent core 28 may comprise at least 2 substantially absorbent material free areas 26 symmetrically disposed on both sides of the longitudinal axis of the absorbent core 28.

The substantially absorbent material free area(s) 26 may be straight and completely oriented longitudinally and parallel to the longitudinal axis but also may be curved or have one or more curved portions.

Furthermore, in order to reduce the risk of liquid bodily exudate leakages, the substantially absorbent material free area(s) 26 advantageously do not extend up to any of the edges of the absorbent material deposition area, and are therefore surrounded by and fully encompassed within the absorbent material deposition area of the absorbent core 28. Typically, the smallest distance between a substantially absorbent material free area 26 and the closest edge of the absorbent material deposition area is at least 5 mm.

"Airfelt-free" absorbent cores 28 comprising substantially absorbent material free areas 26 have been proposed, see for example in EP Patent Application No. 12196341.7.

One or more channel(s) 26' along the substantially absorbent material free area(s) 26 in the absorbent core 28 may start forming when the absorbent material 60 absorbs a liquid and starts swelling. As the absorbent core 28 absorbs more liquid, the depressions within the absorbent core 28 formed by the channel(s) 26' will become deeper and more apparent to the eye and the touch. The formation of the channel(s) 26' may also serve to indicate that the absorbent article 20 has been loaded with liquid bodily exudates. The core wrap bond(s) 27 should remain substantially intact at least during a first phase as the absorbent material 60 absorbs a moderate quantity of liquid bodily exudates.

Figure 5:
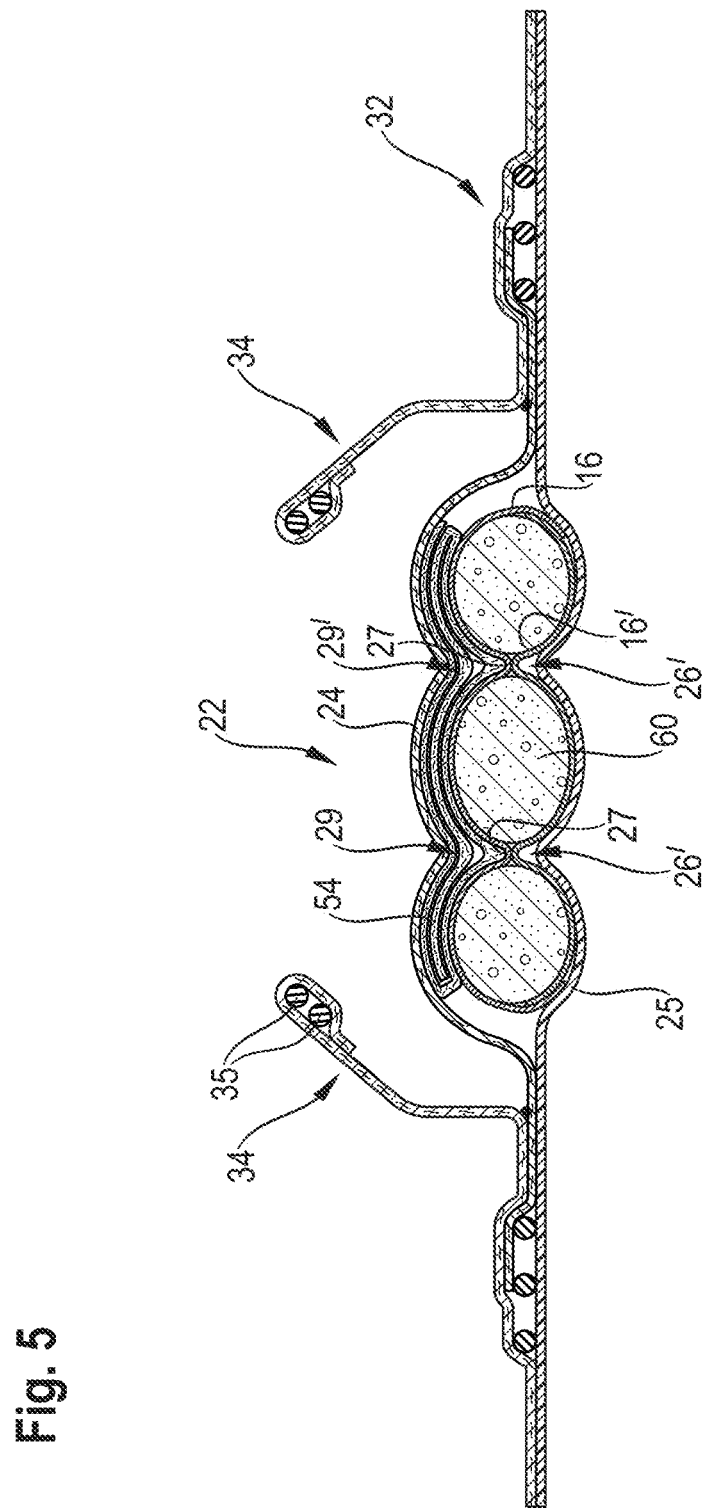
FIG. 5 is a transversal cross-section of the absorbent article of FIG. 3 taken at the same point as FIG. 4 where channels have formed as a result the absorbent article being loaded with liquid bodily exudates.

As shown in FIG. 5, when the absorbent material swells, the core wrap bonds 27 remain at least initially attached in the substantially absorbent material free areas 26. The absorbent material 60 swells in the rest of the absorbent core 28 when it absorbs a liquid, so that the core wrap thus forms channels 26' along the substantially absorbent material free areas 26 comprising the core wrap bonds 27.

When the absorbent material 60 in the absorbent core 28 swells, so that the channels 26' forms, the surface of the top side 16 of the core wrap becomes uneven, see FIG. 5. As the distribution material 54 is placed on top of the top side 16 of the core wrap, the distribution material 54 follows the uneven surface of the top side 16. The formation of the channels 26' creates indentations where portions of the distribution material 54 sink into these indentations. This might promote the formation of disruptions of the distribution material 54, especially when the distribution material 54 is air laid and in a wet state during use. Hence, "airfelt-free" absorbent core 28 comprising substantially absorbent material free areas 26 might promote more disruptions in the distribution material 54 when the absorbent material 60 swells.

A distribution material 54 comprising a fibrous structure consisting of wet-laid fibers and having sufficient wet burst strength, especially a fibrous structure having a wet burst strength from 50 g to 500 g or from 250 g to 350 g or from to 300 g to 350 g according to the Wet Burst Test Method as disclosed herein, may provide a more wet integrate distribution material.

Distribution Material 54

The absorbent article 20 comprises a distribution material 54 between the topsheet 24 and the absorbent core 28. The distribution material 54 is notionally divided in a front region 541, a back region 542 and a middle region 543 located between the front and the back region. Each of the front, back and middle region is ⅓ of the length of the distribution material 54.

The distribution material 54 has a longitudinal axis which may coincide with the longitudinal axis 80 of the absorbent article and a transversal axis (both not shown). The intersection of the longitudinal and transversal axis of the distribution material defines the center of the distribution material 54. The distribution material 54 comprises a front edge, a back edge, and two longitudinal side edges.

Wet-laid Fibers

At least one of the front, back and middle regions (541, 542, 543) of the distribution material 54 comprises one or more layers. The one or more layers of the distribution material 54 comprise a fibrous structure 55 made of wet-laid fibers.

At least in the middle region 543 of the distribution material 54, the distribution material 54 may have from 2 to 10 layers or from 2 to 5 layers. Each layer of the distribution material 54 may comprise a fibrous structure 55 made of wet-laid fibers.

The one or more layers of the distribution material 54 may not comprise air-laid fibers.

The wet-laid fibers may be made of cellulosic fibers. The wet-laid fibers may be produced by forming a predominantly aqueous slurry comprising 95% to 99.9% water. The non-aqueous component of the slurry used to make the wet-laid fibers can comprise from 5% to 80% of *eucalyptus* fibers by weight of the non-aqueous components of the slurry. The non-aqueous components may comprise from 8% to 60% of *eucalyptus* fibers by weight of the non-aqueous components of the slurry, or from 15% to 30% of *eucalyptus* fibers by weight of the non-aqueous component of the slurry. The slurry may comprise from 45% to 60% of Northern Softwood Kraft fibers with up to 20% Southern Softwood Kraft co-refined together, from 25% to 35% unrefined *Eucalyptus* fibers and from 5% to 30% of either repulped product broke or thermo-mechanical pulp.

The wet-laid fibers may comprise a mixture of at least two different materials wherein at least one of the materials comprises a non-naturally occurring fiber, such as a polypropylene fiber, and at least one other material, different from the first material, comprising a solid additive, such as another fiber and/or a particulate.

Synthetic fibers useful herein include any material, such as, but not limited to polymers, those selected from the group consisting of polyesters, polypropylenes, polyethylenes, polyethers, polyamides, polyhydroxyalkanoates, polysaccharides, and combinations thereof. More specifically, the material of the polymer segment may be selected from the group consisting of poly(ethylene terephthalate), poly (butylene terephthalate), poly(1,4-cyclohexylenedimethylene terephthalate), isophthalic acid copolymers (e.g., terephthalate cyclohexylene-dimethylene isophthalate copolymer), ethylene glycol copolymers (e.g., ethylene terephthalate cyclohexylene-dimethylene copolymer), polycaprolactone, poly(hydroxyl ether ester), poly(hydroxyl ether amide), polyesteramide, poly(lactic acid), polyhydroxybutyrate, and combinations thereof.

Further, the synthetic fibers can be a single component (i.e., single synthetic material or a mixture to make up the entire fiber), multi-component such as bi-component (i.e., the fiber is divided into regions, the regions including two or more different synthetic materials or mixtures thereof) and combinations thereof. Nonlimiting examples of suitable bicomponent fibers are fibers made of copolymers of polyester (polyethylene terephthalate/isophtalate/polyester (polyethylene terephtalate) otherwise known as "CoPET/PET" fibers, which are commercially available from Fiber Innovation Technology, Inc., Johnson City, Tenn.

Optional Ingredients

To enhance permanent wet strength, cationic wet strength resins may be optionally added to the papermaking furnish or to the embryonic web. The fibrous structure made of wet-laid fibers may comprise one or more cationic wet strength resins selected from the group consisting of a base activated epoxide polyamide epichlorohydrin resin, an urea-formaldehyde resin, a melamine formaldehyde resin, a polyamide-epichlorohydrin resin, a polyethyleneimine resin, a polyacrylamide resin, a dialdehyde starch and mixtures thereof.

From 0.90 kg/ton to 2.27 kg/ton of dry paper fibers of the cationic wet strength resin may be used, or from 0.22 kg/ton to 13.6 kg/ton, or from 4.53 kg/ton to 11.34 kg/ton of dry paper fibers of the cationic wet strength resin may be used.

The cationic wet strength resins may include cationic water soluble resins. These resins improve wet strength to paper sheets. This resin may improve either temporary or permanent wet strength to the sheet.

KYMENE® resins obtainable from Hercules Inc., Wilmington, Del. may be used, including KYMENE® 736 which is a polyethyleneimine (PEI) wet strength polymer. It is believed that the PEI may improve wet strength by ionic bonding with the pulps carboxyl sites.

KYMENE® 557LX is polyamide epichlorohydrin (PAE) wet strength polymer. It is believed that the PAE contains cationic sites that may lead to resin retention by forming an ionic bond with the carboxyl sites on the pulp. The polymer contains 3-azetidinium groups which react to form covalent bonds with the pulps' carboxyl sites as well as with the polymer backbone. The product may undergo curing in the form of heat or undergo natural aging for the reaction of the azentidinium group.

KYMENE® 450 is a base activated epoxide polyamide epichlorohydrin polymer. It is theorized that like KYMENE® 557LX the resin attaches itself ionically to the pulps' carboxyl sites. The epoxide group is much more reactive than the azentidinium group. The epoxide group reacts with both the hydroxyl and carboxyl sites on the pulp, thereby giving higher wet strengths. The epoxide group can also crosslink to the polymer backbone.

KYMENE® 2064 is also a base activated epoxide polyamide epichlorohydrin polymer. It is theorized that KYMENE® 2064 may improve its wet strength by the same mechanism as KYMENE® 450. KYMENE® 2064 differs in that the polymer backbond contains more epoxide functional groups than does KYMENE® 450. Both KYMENE® 450 and KYMENE® 2064 may require curing in the form of heat or natural aging to fully react all the epoxide groups, however, due to the reactiveness of the epoxide group, the majority of the groups (80-90%) react and improve wet strength off the paper machine.

Mixtures of the foregoing may be used. Other suitable types of such resins include urea-formaldehyde resins, melamine formaldehyde resins, polyamide-epichlorohydrin resins, polyethyleneimine resins, polyacrylamide resins, dialdehyde starches, and mixtures thereof. Other suitable types of such resins are described in U.S. Pat. No. 3,700,623, issued Oct. 24, 1972; U.S. Pat. No. 3,772,076, issued Nov. 13, 1973; U.S. Pat. No. 4,557,801, issued Dec. 10, 1985 and U.S. Pat. No. 4,391,878, issued Jul. 5, 1983.

The cationic wet strength resin may be added at any point in the processes, where it will come in contact with the paper fibers prior to forming the wet web.

Pattern

Figure 6:
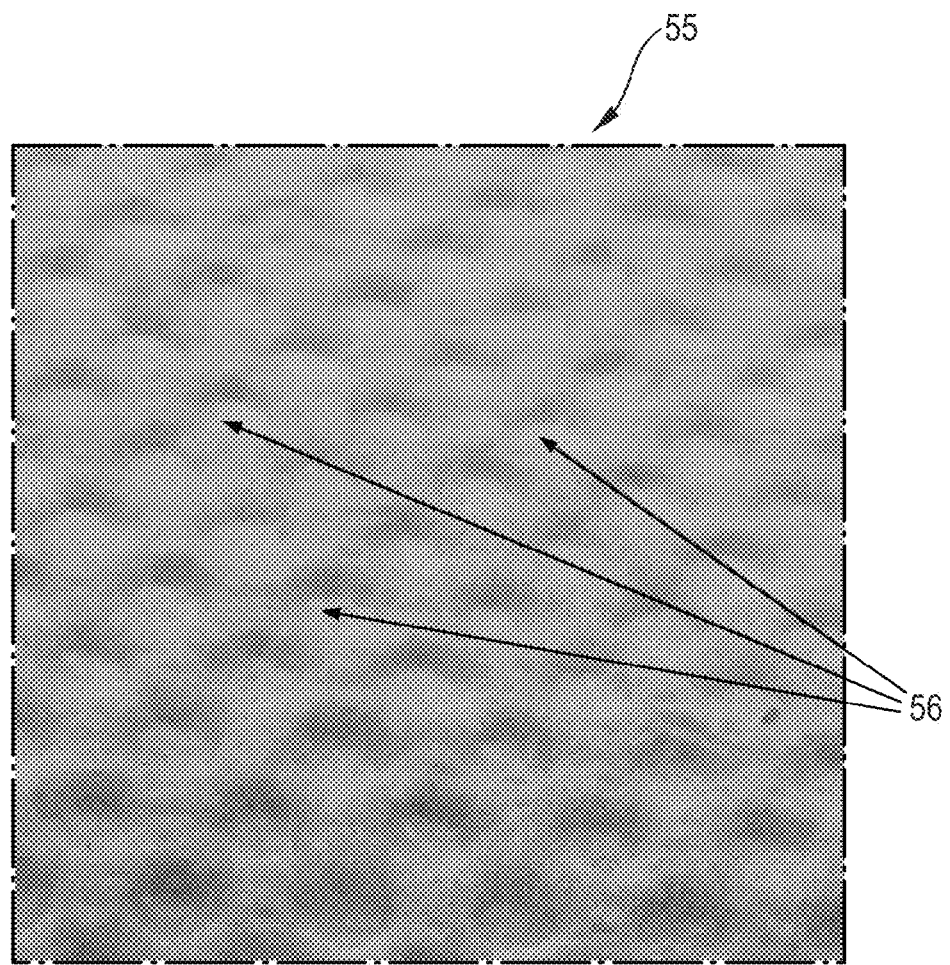
FIG. 6 is an enlarged photographic view of a layer of the distribution material in accordance with the present invention.

Each layer of the distribution material 54 may comprise a pattern of raised elements 56. The one or more layers of the distribution material 54 comprise the fibrous structure 55 made of wet-laid fibers. The fibrous structure 55 may comprise the pattern of raised elements 56, as shown in FIG. 6.

The fibrous structures of the present invention can be made by using a patterned papermaking belt 200 for forming three-dimensionally structured wet-laid webs as described in U.S. Pat. No. 4,637,859, issued Jan. 20, 1987, to Trokhan. Broadly, the papermaking belt of the present invention includes a reinforcing element 202 (such as a woven belt) which can be thoroughly coated with a liquid photosensitive polymeric resin to a preselected thickness. A film incorporating the pattern desired is juxtaposed on the liquid photosensitive resin. The resin is then exposed to light of an appropriate wave length through the film. This exposure to light causes curing of the resin in the exposed areas (i.e., white portions or non-printed portions in the film). Unexposed (and uncured) resin (under the black portions or printed portions in the film) is removed from the system leaving behind the cured resin forming the pattern desired, which pattern transfers during the wet-forming phase of papermaking to the fibrous structure 55.

The fibrous structure 55 can be formed using a patterned papermaking belt 200 having a plurality of raised portions 58, each raised portion 58 forming a corresponding raised element 56 on the fibrous structure 55. Each raised element 56 corresponds thus to a raised portion 58.

Figure 7:
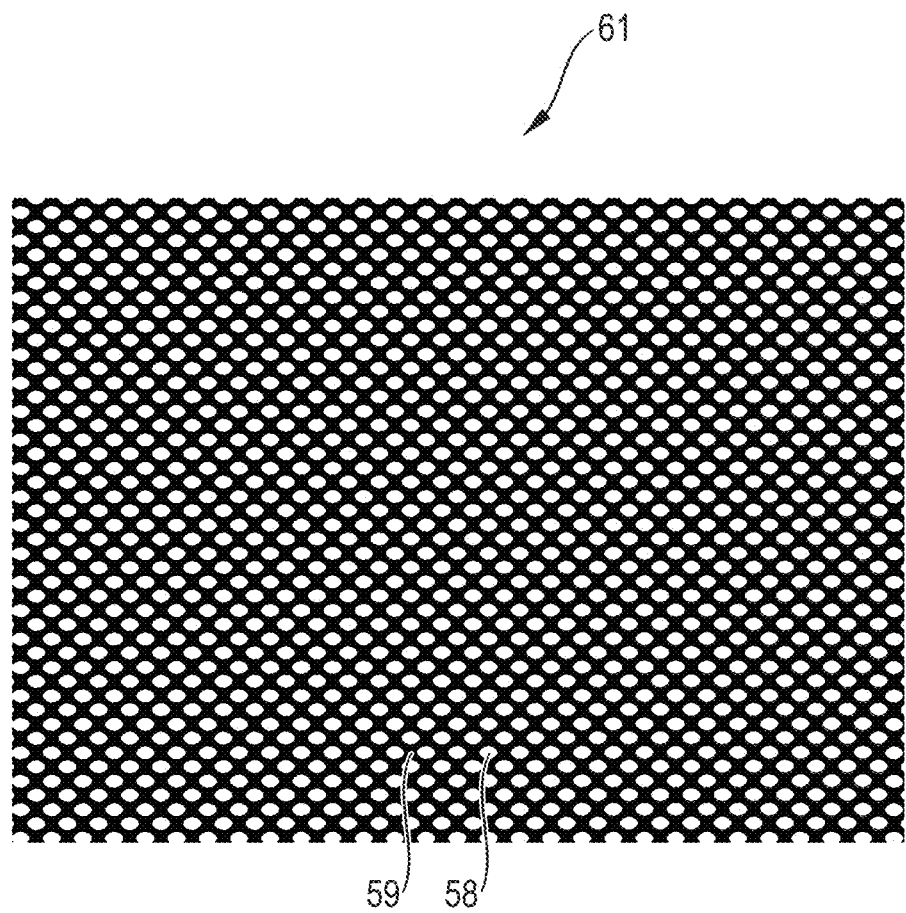
FIG. 7 is an illustration of a portion of a pattern used to make the molding member for making a fibrous structure for the distribution material of the present invention.

Each raised portion 58 of the papermaking belt 200 can be surrounded by the substantially continuous deflection conduit 59, cured from a patterned film 61, as shown in FIG. 7. Any portion of the patterned film 61 shown in FIG. 7 that is black represents a portion of the patterned papermaking belt 200 which is substantially resin free, while any portion of the pattern that is white represents a portion of patterned papermaking belt 200 where resin was cured, and which can be used to form the pattern of raised elements 56.

Figure 9:
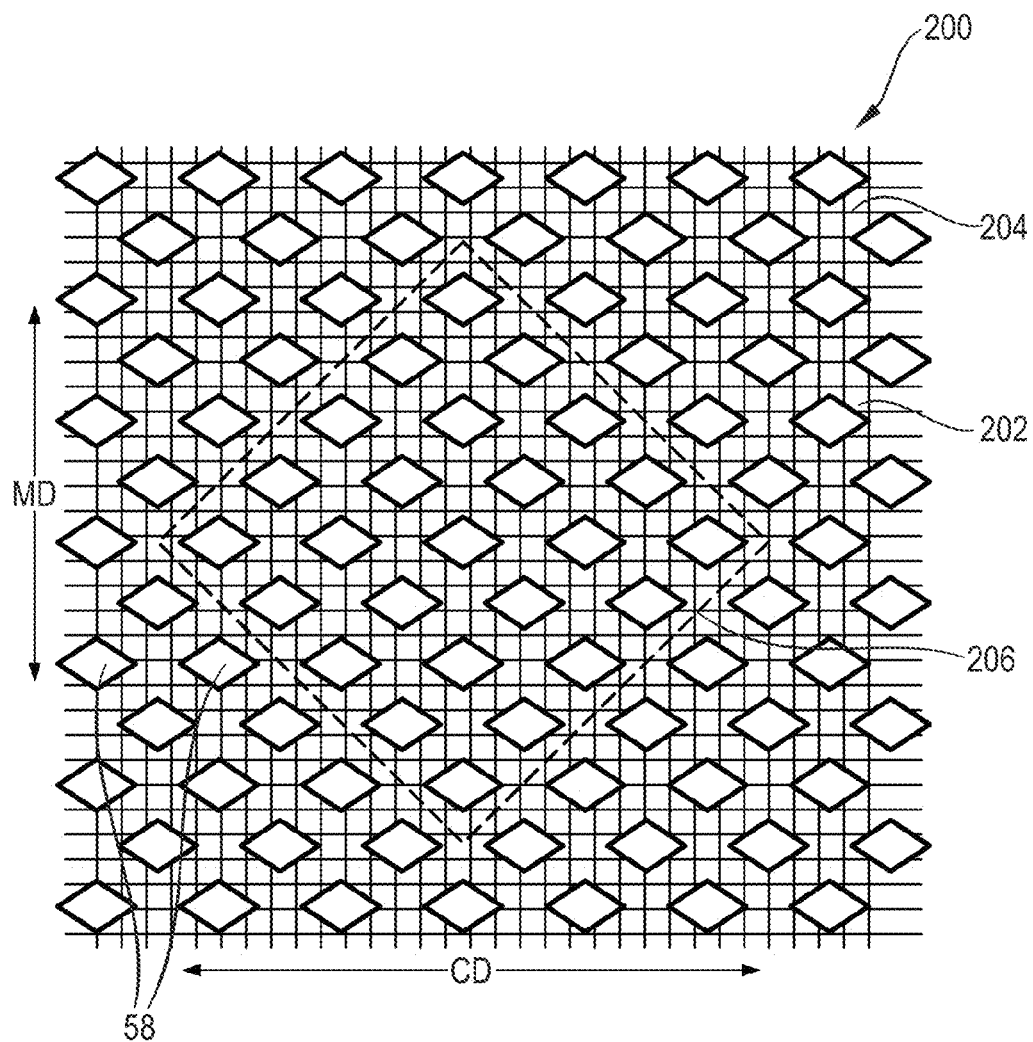
FIG. 9 is a plan view of a portion of a molding member of a papermaking belt of the present invention.

The pattern of FIG. 7 can be exemplary used to form a papermaking belt 200 as shown in FIG. 9. FIG. 9 is a top view showing one unit 206 (shown by dashed line) of one example of a pattern of the papermaking belt 200. The papermaking belt 200 comprises a surface 204. The papermaking belt 200 has a plurality of raised portions 58 extending from the reinforcing element 202 on the papermaking belt 200, wherein the raised portions 58 can be surrounded by a substantially continuous deflection conduit 59. The papermaking belts of the present disclosure and the process of making them are described in US2013/0209749A1 (Myangiro).

Figure 8:
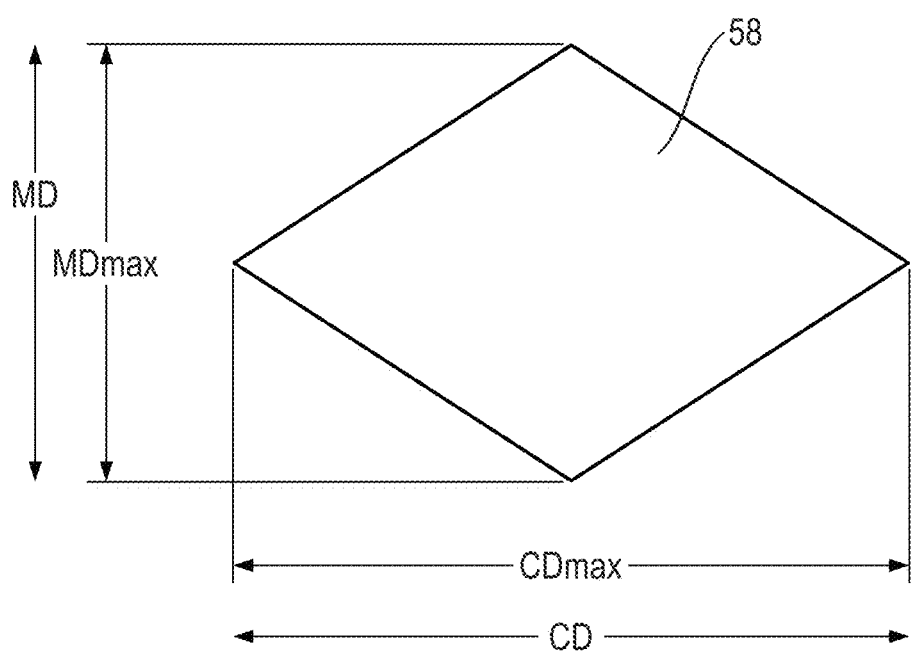
FIG. 8 is a plan view of an example of a raised portion of a molding member for making a fibrous structure of the present invention.

Referring to FIG. 8, each individual raised portion 58 on the papermaking belt 200, or each individual raised element 56 of the fibrous structure 55 (illustrated without the belt or the fibrous structure, respectively, for clarity), can be of any shape, such as a generally elongated shape having a major axis, CDmax, and a minor axis, MDmax. As shown in FIG. 8, individual raised portions 58 can have a rhomboid shape. In general, the dimensions of the raised elements 56 of the fibrous structure 55 are determined by the dimensions of the corresponding raised portions 58 that formed them. That is, the fibrous structure 55 is generally formed over the three-dimensional structure of the papermaking belt 200, so that in one sense the fibers are formed over, or molded to, the raised portions 58. In either case, whether raised portion 58 or raised element 56, the ratio of the length major axis, CDmax, to the length of the minor axis, MDmax, may be greater than or equal to one. Stated another way, the major axis, CDmax, may be longer than or can have the same length as the minor axis, MDmax. The ratio of the length of the major axis, CDmax, to the length of the minor axis, MDmax, may be in the range of 1 to 3 or in the range of 1 to 4 or more.

The CDmax of one raised portion 58 may be comprised between 1.50 mm to 3.50 mm or 1.55 mm to 2.00 mm or 1.53 mm and 2.29 mm, and the MDmax of one raised portion 58 may be comprised between 0.80 mm to 2.00 mm or 1.00 to 1.70 mm or 1.01 mm and 1.53 mm.

The one or more layers of the distribution material 54 may comprise a pattern of raised elements 56. An infinite variety of geometries for each raised element 56 may be possible, as described in U.S. Pat. No. 4,637,859, issued Jan. 20, 1987, to Trokhan. Practical shape of each raised element 56 may include circles, ellipses, ovals, and polygons of three or more sides such as squares, rectangles. There is no requirement that the raised elements 56 be regular polygons or that the sides of the raised elements 56 be straight. The raised elements 56 may comprise curved sides, such as trilobal figures.

Each raised element 56 may be a rhomboid. A rhomboid as used herein is a quadrilateral whose opposite sides are parallel and adjacent sides are unequal, and whose angles are not right angles. Each raised element 56 may be a rhomboid having a first and second diagonal. The first diagonal distance of each raised element 56 may have a length between 1.53 mm and 2.29 mm, and the second diagonal distance of each raised element 56 may have a length between 1.01 mm and 1.53 mm. The first diagonal distance and the second diagonal distance for each raised element 56 may differ from one raised element 56 to another. Alternatively, the first and second diagonal distance of each raised element 56 may be the same in each raised element 56.

Alternatively, each raised portion 58 of the papermaking belt 200 and thus each raised element 56 of the fibrous structure 55 may have other shapes, such as dots, squares, and the like.

Generally, the largest dimension of the raised element 56 may be more than 0.5 mm, or more than 0.8 mm but may be less than 10.0 mm, or less than 5.0 mm. Also, the shortest dimension of the raised element 56 may be more than 0.5 mm, or more than 0.8 mm but may be less than 10.0 mm, or less than 5.0 mm. The largest and the shortest dimension of the raised element 56 can be the same.

Process

The fibrous structure 55 of the present invention can be made on a papermaking belt 200 as described above. US2013/0209749A1 (Myangiro) describes a method for making a fibrous structure of the present invention utilizing a papermaking belt 200, or "molding member," as described above.

Figure 10:
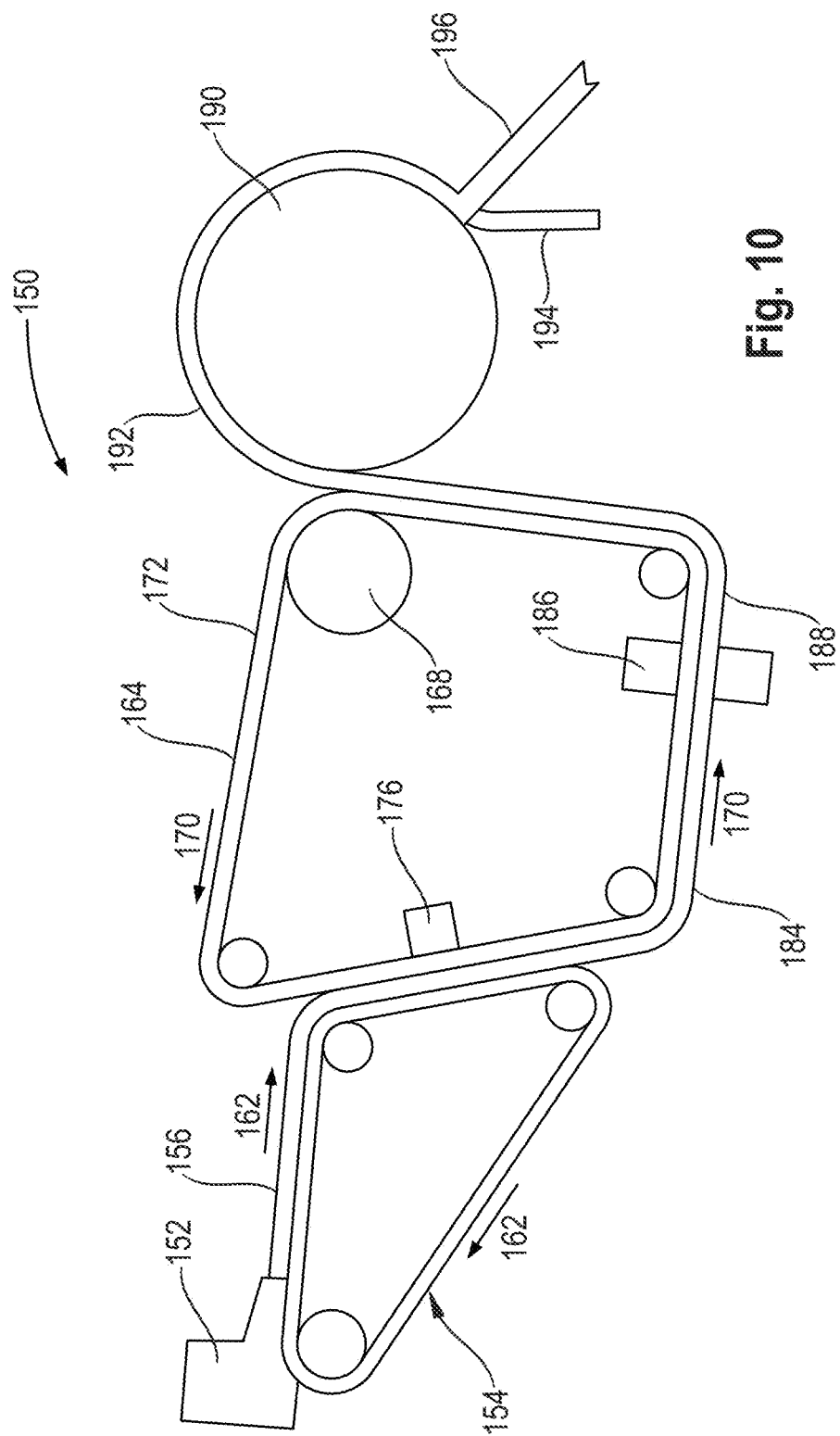
FIG. 10 is a schematic representation of a papermaking apparatus for using a papermaking belt of the present invention and for making a fibrous structure of the present invention.

FIG. 10 is a simplified, schematic representation of one example of a continuous fibrous structure making process and machine useful in the practice of the present disclosure.

As shown in FIG. 10, one example of a process and equipment, represented as 150, for making the fibrous structure 55 of the present invention comprises supplying an aqueous dispersion of fibers to a headbox 152. From the headbox 152, the aqueous dispersion of fibers can be delivered to a foraminous member 154 to produce an embryonic fibrous web 156. The foraminous member 154 can be propelled in the direction indicated by directional arrow 162 by a drive means, not illustrated.

After the aqueous dispersion of fibers is deposited onto the foraminous member 154, the embryonic fibrous web 156 is formed, typically by the removal of a portion of the aqueous dispersing medium by techniques known to those skilled in the art. The embryonic fibrous web 156 can travel with the foraminous member 154 about return roll and can be brought into contact with a molding member 164, also referred to as a papermaking belt. While in contact with the molding member 164, the embryonic fibrous web 156 can be deflected, rearranged, and/or further dewatered.

The molding member 164 can be in the form of an endless belt and can travel in the direction indicated by directional arrow 170. The molding member 164 can be constructed in such a manner that when water is caused to be removed from the embryonic fibrous web 156, as by the application of differential fluid pressure, such as by a vacuum box 176, and when the water is removed from the embryonic fibrous web 156 in the direction of the molding member 164, the water can be discharged from the system without having to again contact the embryonic fibrous web 156 in either the liquid or the vapor state. A first surface 172 of the molding member 164 can comprise one or more raised portions 58.

After the embryonic fibrous web 156 has been associated with the molding member 164, wet-laid fibers within the embryonic fibrous web 156 are deflected into the continuous or substantially continuous deflection conduits 59 present in the molding member 164 to lead to an intermediate fibrous web 184.

The intermediate fibrous web 184 may first pass through an optional predryer 186. The predryer 186 may be a conventional flow-through dryer (hot air dryer) known to those skilled in the art. The predried fibrous web 188 travels to an impression nip roll 168. As the predried fibrous web 188 passes through the nip formed between impression nip roll 168 and a surface of a Yankee dryer 190, the pattern formed by the top surface 172 of the molding member 164 is impressed into the predried fibrous web 188 to form a pattern of raised elements 56 imprinted in the fibrous web 192.

The imprinted fibrous web 192 may then be foreshortened by creping the web 192 with a creping blade 194 to remove the web 192 from the surface of the Yankee dryer 190 resulting in the production of a creped fibrous structure 196. The fibrous structure 55 may be wound in a roll.

Wet Burst Strength/Total Dry Tensile Strength

The fibrous structure 55 may be unwound from a roll and cut into a plurality of sheets. The distribution material 54 may be made of at least one sheet of the fibrous structure 55 which has been subsequently folded to form more than one layer.

The one or more layers of the distribution material 54 has a Wet Burst Strength from 50 g to 500 g or from 250 g to 350 g or from to 300 g to 350 g according to the Wet Burst Test Method as disclosed herein. Further, each layer may have a Total Dry Tensile strength from 315 $g/cm^2$ to 945 $g/cm^2$ according to the Total Dry Tensile Strength Test Method as disclosed herein.

Construction of the Distribution Material 54

At least one of the front, back and middle regions (541, 542, 543) of the distribution material 54 comprises one or more layers. The one or more layers of the distribution material 54 comprise a fibrous structure 55 made of wet-laid fibers.

At least in the middle region 543 of the distribution material 54, the distribution material 54 may comprise from 2 to 10 layers or from 2 to 5 layers.

The front and/or back region 541, 542 of the distribution material 54 or a portion of the front and/or back region 541, 542 may also have from 1 to 10 layers or from 2 to 10 layers or from 2 to 5 layers. The front region 541 or a portion thereof may have the same number of layers as the back region 542 or a portion thereof or may have a different number of layers. The front and back regions 541, 542 or portions thereof, and the middle region 543 may have the same number of layers.

Alternatively, only the middle region 543 of the distribution material 54 may have from 2 to 10 layers while the front and back region 541, 542 have only one layer. Still alternatively, the middle region 543 and one or a portion of the front and back regions 541, 542 or a portion of one of the front and the back regions 541, 542 may have from 2 to 10 layers, while the respective other region (i.e. the front or back region 541, 542) has only one layer.

The number of layers do not have to be the same throughout the front, back and middle region 541, 542 and 543 as long as the middle region 543 of the distribution material 54 has from 2 to 10 layers everywhere across the middle region 543. However, the number of layers may be the same throughout the front, back and middle region 541, 542, 543.

The smallest transversal dimension of the middle region 543 may be at least 30% or at least 50% of the transversal dimension of the narrowest width of the absorbent article 20.

The one or more layers of the distribution material 54 comprise a fibrous structure 55 made of wet-laid fibers. The one or more layers of the distribution material 54 exhibit a Wet Burst Strength from 50 g to 500 g or from 250 g to 350 g or from to 300 g to 350 g according to the Wet Burst Test Method as disclosed herein. The one or more layers of the distribution material 54 have a dry caliper at a pressure of 2.06 kPa from 0.1 mm to 1.0 mm or from 0.5 mm to 1.0 mm and the one or more layers of the distribution material 54 have a total dry caliper at a pressure of 2.06 kPa from 1.0 mm to 30.0 mm according to Dry Caliper measurement Test Method.

The one or more layers of the distribution material 54 may comprise a pattern of raised elements 56 as set out above.

The one or more layers of the distribution material 54 may exhibit a basis weight from 10 to 200 gsm or from 10 to 60 gsm or from 20 to 50 gsm. At least in the middle region 543 of the distribution material 54, the distribution material 54 may comprise from 2 to 10 layers or from 2 to 5 layers. The middle region 543 of the distribution material 54 may have an overall basis weight from 50 to 500 gsm or from 50 to 250 gsm or from 100 to 150 gsm. Each layer may have a dry caliper at a pressure of 2.06 kPa from 0.1 mm to 1.0 mm or from 0.5 mm to 1.0 mm and the middle region of the distribution material 54 may have a total dry caliper at a pressure of 2.06 kPa from 1.0 mm to 30.0 mm according to Dry Caliper measurement Test Method.

Figure 11A:
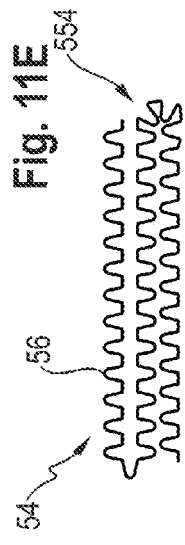
FIG. 11A is an exemplary distribution material according to the present invention.

Each layer of the distribution material 54 may have different sizes such as different longitudinal and/or transversal dimension. Incorporating layers with different sizes in the distribution material 54 enables profiling the basis weight and overall dry caliper of the distribution material 54 at certain locations of the absorbent article 20. For instance, some areas of the middle region may have more layers that other areas of the middle region, as long as the overall middle region can have from 1 to 10 layers or from 2 to 10 layers everywhere. FIG. 11A shows an example of a distribution material 54 comprising three layers. Each layer consists of the fibrous structure 55 and comprises a pattern of raised elements 56.

At least in the middle region 543 of the distribution material 54, the distribution material 54 may have from 1 to 10 layers or from 2 to 10 layers or from 2 to 5 layers. The distribution material 54 may include void spaces due to the pattern of the raised elements, the spaces between the different layers of the distribution material 54 and the porosity of each layer. Having at least in the middle region 543, 1 to 10 or 2 to 10 layers provides the void spaces needed to drain the liquid bodily exudates from the topsheet 24, distribute and transfer them to the absorbent core 28.

1 to 10 layers or 2 to 10 layers or 2 to 5 layers may be only located in the middle region 543 of the distribution material 54. Hence, there may be more layers of fibrous structure 55 in the middle region 543 of the distribution material 54, and thus more available void spaces in the middle region 543 than in the front and back region 541, 542 of the distribution material 54. The liquid bodily exudates may thus be efficiently drained from the topsheet 24 to the middle region 543 and then distributed and transferred to the absorbent core 28.

The center of the distribution material 54 may coincide with the center of the absorbent article 20 where the longitudinal axis 80 and the transversal axis 90 intersect.

Alternatively, the distribution material 54 can be shifted towards the front region 36 of the absorbent article 20. The center of the distribution material 54 can be shifted along the longitudinal axis 80 of the absorbent article 20 towards the front edge 10 of the absorbent article 20 such that the center of the distribution material 54 is positioned towards the front region 36 of the absorbent article 20 relative to the center of the absorbent article 20. The center of the distribution material 54 may be shifted by 10% or by 20% of the length of the absorbent article 20 towards the front edge 10 of the absorbent article 20.

The center of the distribution material 54 will thus be positioned in a location which may coincide more efficiently to the pee point of the wearer.

Alternatively, 1 to 10 layers or 2 to 10 layers or 2 to 5 layers may also be located in the front and/or back region 541, 542 of the distribution material 54, and the front and/or back region 541, 542 of the distribution material 54 have an overall basis weight from 50 to 250 gsm and a total dry caliper at a pressure of 2.06 kPa from 1.0 mm to 30.0 mm according to Dry Caliper measurement Test Method. The front and/or back region 541, 542 may thus more efficiently assist in draining the liquid bodily exudates.

A distribution material made of unconsolidated air-laid fibers may form some cracks and disruptions especially in the wet state during use. These disruptions are mainly due to the fact that the unconsolidated air-laid fibers might not be able to provide enough wet integrity. Undesired randomly positioned liquid channels in the distribution material 54 might occur. The liquid bodily exudates might be routed through these liquid channels directly to the absorbent core 28. As a consequence, the liquid bodily exudates might not be efficiently distributed in the distribution material 54. Moreover, these uncontrolled disruptions are perceived as sign of lower product quality from many consumers.

In the case of the fibrous structure 55 made of wet-laid fibers, the fibrous structure has an improved cohesive structure compared to unconsolidated air-laid fibers. Due to the wet-laid papermaking process as described above, the wet-laid fibers relatively strongly adhere to each other. The fibrous structure 55 is thus less prone to form disruptions when wetted. Hence, each layer of the distribution material 54 which consists of the fibrous structure 55 has an improved wet integrity. The liquid bodily exudates are therefore efficiently distributed in the distribution material before being transferred to the absorbent core 28.

Also, the one or more layers of the distribution material 54 may have a pattern of raised elements 56.

The raised elements 56 of the pattern of raised elements 56 may protrude from each layer of the distribution material 54 towards the topsheet 24 or the raised elements 56 of the pattern of raised elements 56 may protrude from each layer of the distribution material 54 towards the absorbent core 28.

Alternatively, the raised elements 56 of the pattern of raised elements 56 of one or more layers may protrude towards the topsheet 24 and the raised elements 56 of the pattern of raised elements 56 of one or more other layers may protrude towards the absorbent core 28.

Each layer of the distribution material 54 may therefore have a tridimensional structure. The tri-dimensional structure which results from the wet-laid papermaking process can help reinforcing the wet integrity of the fibrous structure 55. The cohesive structure of the distribution material 54 can be due to how the wet-laid fibers adhere to each other and also to the tridimensional structure of each layer. The cohesive structure can provide a much more compact distribution material 54 than a distribution material made of air-laid fibers.

In contrast with a distribution material 54 made of air-laid fibers, the distribution material 54 of the present invention may be specially designed to provide a specific feature. For example, the distribution material 54 may be printed. Having the distribution material 54 printed may provide a visual signal to the caregiver from the topsheet 24. A visual signal might help indicating the absorbency capacity of the absorbent article 20. A visual signal might help the consumer to use the appropriate absorbent article 20 at the appropriate time, e.g. daytime wear or more absorbent overnight wear.

In addition or instead of printing, the distribution material 54 may be embossed. Embossing the distribution material 54 may help improving the depth perception when viewing from above the topsheet 24.

Figure 11B:
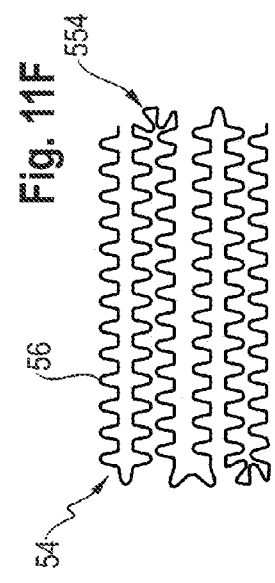
FIG. 11B is an exemplary distribution material according to the present invention.

At least the 2 to 10 layers of the distribution material 54 at least in one of the front, back and middle regions (541, 542, 543) or at least in the middle region 543 of the distribution material 54 may be provided by folding at least one sheet of the fibrous structure 55 to form at least some of the 2 to 10 layers. FIG. 11B shows a first sheet 551 of the fibrous structure 55 which has been trifolded and placed on top of one single layer of a second sheet 552 of the fibrous structure 55.

Figure 11C:
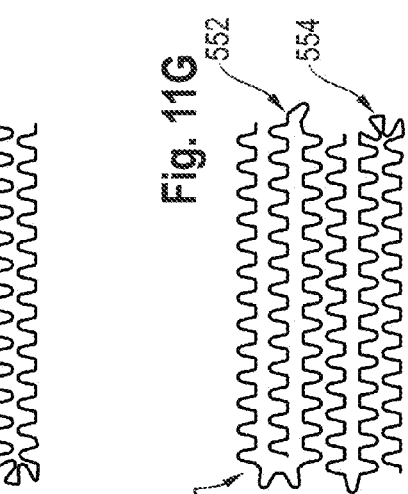
FIG. 11C is an exemplary distribution material according to the present invention.
Figure 11D:
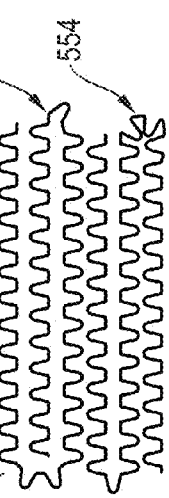
FIG. 11D is an exemplary distribution material according to the present invention.

The distribution material 54 may consist of one sheet 552 of the fibrous structure 55 which is folded at least in one of the front, back and middle regions (541, 542, 543) or at least in the middle region 543 of the distribution material 54 to obtain from 2 to 10 layers or from 2 to 5 layers. FIG. 11C and FIG. 11D respectively give an example of a distribution material 54 which consists of a sheet 552 of the fibrous structure which comprises either 3 layers or 5 layers.

As shown in FIGS. 11B and 11C, the sheet 552 of the fibrous structure 55 of the distribution material 54 may be notionally divided in three portions. The first portion of the sheet 552 of the fibrous structure 55 may be folded on to the second portion. The third portion of the sheet 552 of the fibrous structure 55 may be then folded onto the folded first portion to form a trifolded sheet of material. In that case, the longitudinal edges of the distribution material 54 might have increased stiffness. However, it may be desirable to have a distribution material 54 which may be stiffer at its longitudinal side edges and softer around the center of the distribution material 54. Otherwise, the longitudinal side edges may be incrementally stretched, slitted or cut to reduce stiffness.

The distribution material may comprise at least one sheet of the fibrous structure which is C-folded or S-folded at least in one of the front, back and middle regions (541, 542, 543) or at least in the middle region 543 of the distribution material 54 to form at least some of the respective 2 layers or from 3 to 10 layers.

Figure 11E:
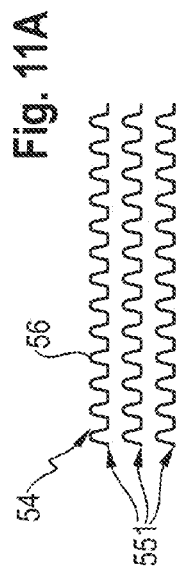
FIG. 11E is an exemplary distribution material according to the present invention.
Figure 11F:
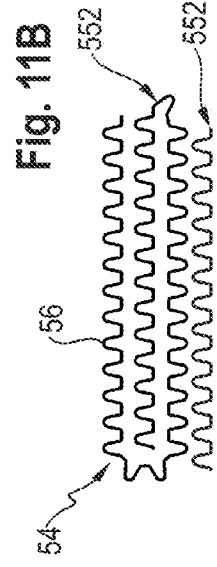
FIG. 11F is an exemplary distribution material according to the present invention.
Figure 11G:
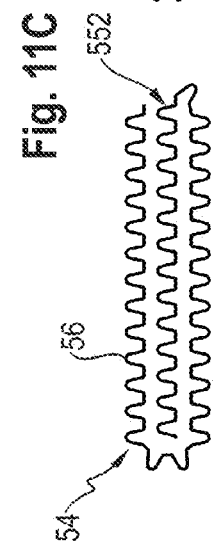
FIG. 11G is an exemplary distribution material according to the present invention.

FIG. 11E shows an example of a sheet 554 of the fibrous structure 55 which has been S-folded to form 3 layers. FIG. 11F shows an example of a sheet 554 of the fibrous structure 55 which has been S-folded to form 6 layers. FIG. 11G shows an example of a distribution material 54 comprising a sheet 554 of the fibrous structure 55 which has been S-folded to form 3 layers. The sheet 554 is placed below a sheet 552 of the fibrous structure 55 which has been trifolded.

Figure 11H:
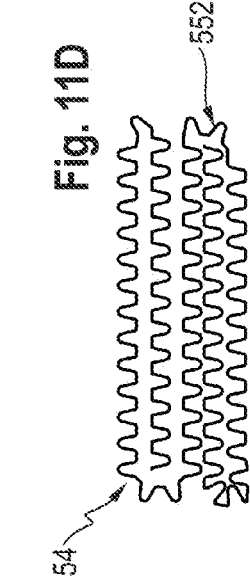
FIG. 11H is an exemplary distribution material according to the present invention.

The raised elements 56 of the pattern of raised elements 56 of one or more layers may protrude towards the topsheet 24 and the raised elements 56 of the pattern of raised elements 56 of one or more other layers may protrude towards the absorbent core 28, as shown in FIG. 11H. As a result, different layers can have inverted tridimensional structures relative to other layers, which might lead to different distributive properties.

As a result, the void spaces created between the raised elements 56, the void spaces between the different layers of the distribution material 54 and also the porosity of each individual layer impact the distributive properties of the distribution material 54.

The distribution material 54 may have a permeability of at least 150 Darcy according to In Plane Radial Permeability Test Method and a Fixed Height Saturation at 5 cm above 40% according to the Fixed Height Saturation Test Method.

The distribution material 54 may have a permeability from 250 to 3000 Darcy, or from 300 to 1000 Darcy according to In Plane Radial Permeability Test Method, as disclosed herein.

The distribution material 54 may have a Fixed Height Saturation at 5 cm above 40%, or above 45% or above 50% up to 90% according to the Fixed Height Saturation Test Method, as disclosed herein.

The distribution material 54 may have a ratio of wet/dry caliper at 2.06 kPa of at least 0.5. The distribution material 54 may have a ratio of dry caliper at 4.82 kPa/2.06 kPa of at least 0.5 or of at least 0.9.

The distribution material 54 may also have different geometries. The shape of the distribution material 54 can vary, in particular it can be rectangular or shaped with a so-called "dog bone" or "hour-glass" shape, which shows a tapering along its width at least in a crotch region of the absorbent article 20.

The distribution material 54 can be facilitated by having one sheet of the fibrous structure 55 having a length L1 and a width W1. Two slits on each longitudinal side of the sheet of the fibrous structure 55 can be introduced across the width direction W1 to create at least a first, second and central subsections 121, 122 and 123, as shown in FIG. 12 A. Each subsection may be folded along the longitudinal axis of the distribution material 54. For example, FIG. 12B shows that the central subsection 123 has been folded while the other first and second subsection 121 and 122 remain unfolded.

The central subsection 123 may coincide with the middle region 543 of the distribution material 54. Alternatively, the central subsection 123 may be larger than the middle region 543 along the longitudinal axis of the distribution material 54.

A top portion of the distribution material 54 may be attached to the topsheet 24 or to any layer, e.g. an acquisition layer 52 which is positioned between the topsheet 24 and the distribution material 54. A bottom portion of the distribution material 54 may be attached to the substrate of the absorbent core 28 facing the topsheet 24 or to any layer between the distribution material 54 and the substrate of the absorbent core 28 facing the topsheet 24. The bottom portion of the distribution material may be attached to the substrate of the absorbent core 28 facing the topsheet 24 which is made of a nonwoven web.

The top portion of the distribution material 54 may be attached to the topsheet 24 or to any layer between the topsheet 24 and the distribution material 54 by a pattern of adhesive. The bottom portion of the distribution material 54 may be attached to the substrate of the absorbent core 28 facing the topsheet 24 or to any layer between the substrate of the absorbent core 28 facing the topsheet 24 and the distribution material 54 by a pattern of adhesive.

The pattern of adhesive may be a plurality of adhesive lines which is parallel to a longitudinal axis 80 of the absorbent article 20 or to a transverse axis 90 of the absorbent article 20.

The pattern of adhesive may be a plurality of overlapping, substantially continuous, semi-cycloidal lines of adhesive extending along the longitudinal direction the absorbent article 20.

The pattern of adhesive may be a plurality of separate lines, such as straight lines, spirals, or may be a plurality of dots of adhesive.

Each layer of the distribution material may be attached to each adjacent layer by a pattern of adhesive. If the adhesive is hydrophobic (e.g. hotmelt adhesive), the liquid bodily exudates might be drained from the distribution material 54 to the absorbent core 28 between the pattern of adhesive.

Each layer of the distribution material 54 may be attached to each adjacent layer with a similar pattern of adhesive, as set out above.

EXAMPLE

The diaper tested in this example was similar to the commercially available Pampers Baby Basics s4 (size 4) diapers currently sold in Germany. However, the absorbent core was replaced by the following absorbent core: The absorbent core contained SAP as absorbent material, without cellulosic fibers. The core wrap comprised two substrates one provided on the top side and the other provided on the bottom side of the core, the upper substrate forming a C-wrap along the longitudinal edges of the core. The core comprised two curved areas free of absorbent material. These areas were symmetric in relation to the longitudinal axis and had a projected length (i.e. the straight distance between the two ends of the curve measured along the longitudinal axis) thereon of 227 mm, a width of 8 mm and a shortest distance from each other of 20 mm. The top and bottom core wrap substrates were further attached to themselves through the substantially absorbent material free areas 26 along substantially the whole length of the areas 26.

The absorbent core comprised in total 12.0 g SAP (available from Nippon Shokubai, Japan) applied in an area of deposition having a length of 360 mm and a width of 110 mm (rectangular profile). The absorbent core was formed by SAP printing technology, as disclosed in US2010/0051166A1, which combines the two nonwoven substrates each supporting a SAP layer. The SAP was the same as it is used in Pampers Active Fit diapers currently commercially available in Germany.

Fibrous hot melt adhesive was applied on the upper substrate 16 before applying the SAP layer, and was coated with 41 lines each 1 mm wide with a distance of 1 mm between the lines along the whole length of the core wrap (390 mm) for a total amount of 0.128 g of adhesive.

Each SAP layer had a microfiber elastic hot melt adhesive applied on top of it to immobilize the SAP layer on the substrate. 0.129 g and 0.172 g of microfiber adhesive, the area of application having a width of 110 mm and length of 390 mm on each SAP layer.

The core wrap had a length of 390 mm with two end flaps free of absorbent material having a length of 15 mm at the back and at the front edge of the absorbent core. The front and back end seals of the core were glued together, the adhesive lines having each a length of 30 mm from the front end seal and 20 mm from the back end seal. The upper substrate 16 was a 8 gsm hydrophilically treated SMMS nonwoven and the lower substrate 16' was a 8 gsm SMMS nonwoven. The upper substrate was cut at a length of 390 mm and a cut width of 165 mm. The lower substrate had a cut length of 390 mm and a cut width of 130 mm. The upper substrate was C-wrapped around the lower substrate on the lateral edges of the core and the lateral edges of the lower layer were slightly formed upwards on the edge of the absorbent material of the core so that the overall width of the folded core wrap was 120 mm. The C-wrap was made permanent by application of a line of adhesive between the substrates, the line having a width of 4 mm and being 390 mm long on each side of the core.

The two substrates were additionally attached together through the channels. The bond was formed by the auxiliary and microfiber adhesive.

Instead of the layer of modified cellulose fibers, which is used as the distribution material in Pampers Baby Basics, the following sheet of fibrous structure was placed between the acquisition layer and the absorbent core.

The distribution material 54 was made of a sheet of fibrous structure. The fibrous structure was made of wet-laid fibers which have been air through dried and made according the process above. The sheet of fibrous structure had a basis weight of 41.8 gsm with a length of 298 mm and a width of 240 mm. The sheet of fibrous structure showed a dry caliper at 2.06 kPa of 0.62 mm according to the Dry Caliper measurement Test Method, a Wet Burst strength of 340 g according to the Wet Burst Test method and a Total Dry Tensile strength of 287 g/cm$^2$ measured according the Total Dry Tensile Strength Test method.

The sheet of the fibrous structure comprised three portions. Each portion had a length of 298 mm and a width of 80 mm. The sheet of fibrous structure was trifolded along its length: A first portion of the sheet was folded on a second portion of the sheet. A third portion of the sheet was folded over the first portion of the sheet. The resulting distribution material had a length of 298 mm and a width of 80 mm. Each folded portion resulted in a layer in the distribution material. Hence, the distribution material had 3 layers in its front, middle and back region.

The resulting distribution material has a dry caliper at 2.06 kPa of 1.81 mm, a dry caliper at 4.82 kPa of 1.71 mm and a wet caliper at 2.06 kPa of 1.72 mm according to the Dry and Wet Caliper measurement Test Method. Accordingly the ratio wet/dry caliper at 2.06 kPa is 0.95 and the ratio of dry caliper at 4.82 kPa/2.06 kPa is 0.94.

The distribution material has a permeability of measured according the IPRP method of 309.0 Darcy and an FHS5 according to the FHS method of 49.4%.

The distribution material has been attached with the third layer (third portion) to the acquisition layer. The distribution material has been attached with the second layer (second portion) to the top side 16 of the core wrap. Hence, the distribution material comprised the third layer facing the topsheet, the second layer facing the absorbent core and the first layer between the third and second layer.

The sheet of the fibrous structure had a pattern of raised elements. The raised elements protruded toward the absorbent core for the first and third layer. The raised elements protruded toward the topsheet for the second layer.

The diaper was subjected to the FLAT Acquisition Test Method as described in EP Patent application 2535698 A1. The Acquisition times were as follows:

| | |
|---|---|
| 1st Gush [s] | 42 |
| 2nd Gush [s] | 41 |
| 3rd Gush [s] | 44 |
| 4th Gush [s] | 99 |

Test Methods

Unless indicated otherwise, all tests described herein are made with samples conditioned at least 24 hours at 21° C.±2° C. and 50%±20% Relative Humidity (RH).

General Sample Preparation:

For the IPRP Test Method and the FSH Test Method described below, an annular or disc sample of the whole distribution material has to be prepared. For this, the center of the annular sample coincides with the center of the distribution material. As set out above, the intersection of the longitudinal and transversal axis of the distribution material defines the center of the distribution material.

Wet Burst Test Method

The Wet Burst Strength as used herein is a measure of the ability of a fibrous structure to absorb energy, when wet and subjected to deformation with regard to the plane of the fibrous structure.

The wet burst strength of a fibrous structure (referred to as "sample" within this test method) is determined using an electronic burst tester and specified test conditions. The results obtained are averaged out of 4 experiments and the wet burst strength is reported for a fibrous structure 55 consisting of one single layer of wet-laid fibers.

Equipment

Apparatus: Burst Tester—Thwing-Albert Vantage Burst Tester or equivalent ball burst instrument where the ball moves downward during testing. Refer to manufacturer's operation and set-up instructions. The ball diameter is 1.59 cm and the clamp opening diameter is 8.9 cm.

Calibration Weights—Refer to manufacturer's Calibration instructions

Conditioned Room Temperature and Humidity controlled within the following limits for Laboratory testing:

Temperature: 23°±1° C.
Relative humidity: 50%±2%
Paper Cutter—Cutting board, 600 mm size
Scissors—100 mm, or larger
Pan—Approximate Width/Length/Depth: 240×300×50 mm, or equivalent
Distilled water at the temperature of the conditioned room used Sample Preparation The fibrous structure 55 may be unwound from the roll.

The samples to be tested are conditioned in the conditioned room for 24 hours immediately before testing. All testing occurs within the conditioned room.

Cut the samples so that they are approximately 228 mm in length and width of approximately 140 mm in width.

Operation

Set-up and calibrate the Burst Tester instrument according to the manufacturer's instructions for the instrument being used.

Holding the sample by the narrow edges, the center of the sample is dipped into a pan filled approximately 25 mm from the top with distilled water. The sample is left in the water for 4 (±0.5) seconds.

The excess water is drained from the sample for 3 (±0.5) seconds holding the sample in a vertical position.

The test should proceed immediately after the drain step. The sample should have no perforations, tears or imperfections in the area of the sample to be tested. If it does, start the test over.

The sample is placed between the upper and lower rings of the Burst Tester instrument. The sample is positioned centered and flat on the lower ring of the sample holding device in a manner such that no slack in the sample is present.

The upper ring of the pneumatic holding device is lowered to secure the sample.

The test is started. The test is over at sample failure (rupture) i.e., when the load falls 20 g from the peak force. The maximum force value is recorded.

The plunger will automatically reverse and return to its original starting position.

The upper ring is raised in order to remove and discard the tested sample.

The procedure is repeated until all replicates have been tested.

Calculation

Wet Burst Strength=sum of peak load readings/number of replicates tested Report the Wet Burst results to the nearest gram.

Dry and Wet Caliper Measurement Test Method at Different Pressures

The intent of this method is to provide a procedure to determine the dry or wet caliper for each layer of the distribution material 54 under predefined pressure. The test can be executed with a conventional caliper micrometer, such as Type DM 2000 available from Wolf-Messtechnik GmbH, Am St. Niclas Schacht 13, Freiberg (Germany), having a circular sample foot of 15 mm diameter, having a weight for the foot of 17.2 g and additional weights of 20.0 g or 69.6 g or 106.9 g in order to achieve a total of 37.2 g or 86.8 g or 124.1 g to adjust the pressure to 2.065 kPa or 4.819 kPa or 6.889 kPa respectively (equivalent to 0.3 psi or 0.7 psi or 1.0 psi).

The caliper of each layer of the distribution material 54 is determined. The total caliper of the distribution material is the sum of the caliper of each layer of the distribution material.

The Dry or Wet Caliper measurement is carried out on the following square samples: of 3 cm centered on one single layer of the distribution material to obtain the caliper of one layer.

Basic Protocol for Dry and Wet Caliper

1. All testing is conducted at 23±1° C. and 50±2% relative humidity.

2. The distribution material is allowed to equilibrate at 23±1° C. and 50±2% relative humidity for 8 hours.
3. The center of the sample is determined as described above and marked on the wearer surface of the sample.
4. The sample is positioned under the caliper gauge with the wearer surface toward the sample contact foot and with the center of the sample centered under the foot.
5. The sample contact foot is gently lowered into contact with the surface of the sample.
6. A Pressure of 2.06 kPa (0.3 psi) or 4.819 kPa (0.7 psi) or 6.889 kPa (1.0 psi) is applied.
7. The caliper reading is taken 2 seconds after the foot comes into contact with the sample.

Specific Step for the Wet Caliper Measurement:

In order to measure the wet caliper, between the steps 3 and 4 set out above, the sample is wetted uniformly with the help of a pipette adding 1.5 g of water per g of sample, and left to equilibrate for 30 seconds.

The caliper is the average of three replicates and is reported in millimeters rounded to the nearest 0.01 mm.

Total Dry Tensile Strength Test Method

The Total Dry Tensile (TDT) Strength of the fibrous structure 55 of the present invention and/or the distribution material comprising such fibrous structure is measured as follows. Strips of the fibrous structure 55 having as a dimension 2.5 cm×12.7 cm are provided. The strip is placed on an electronic tensile tester Model EJA Vantage from the Thwing-Albert Instrument Co. Wet Berlin, N.J., in a conditioned room at a temperature of 28° C.±2.2° C. and a relative humidity of 50%±10%. The crosshead speed of the tensile tester is 10.2 cm/minute and the gauge length is 10.2 cm. The MD and CD tensile strength are reported in $g/cm^2$ and rounded to the nearest $g/cm^2$. The TDT Strength is the arithmetic total of MD and CD tensile strengths of the strips.

In Plane Radial Permeability (IPRP) Test Method

This test is suitable for measurement of the In-Plane Radial Permeability (IPRP) of a porous material. The quantity of a saline solution (0.9% NaCl) flowing radially through an annular sample of the material under constant pressure is measured as a function of time.

Testing is performed at 23° C.±2C.° and a relative humidity 50%±5%. All samples are conditioned in this environment for twenty four (24) hours before testing.

Figure 14:
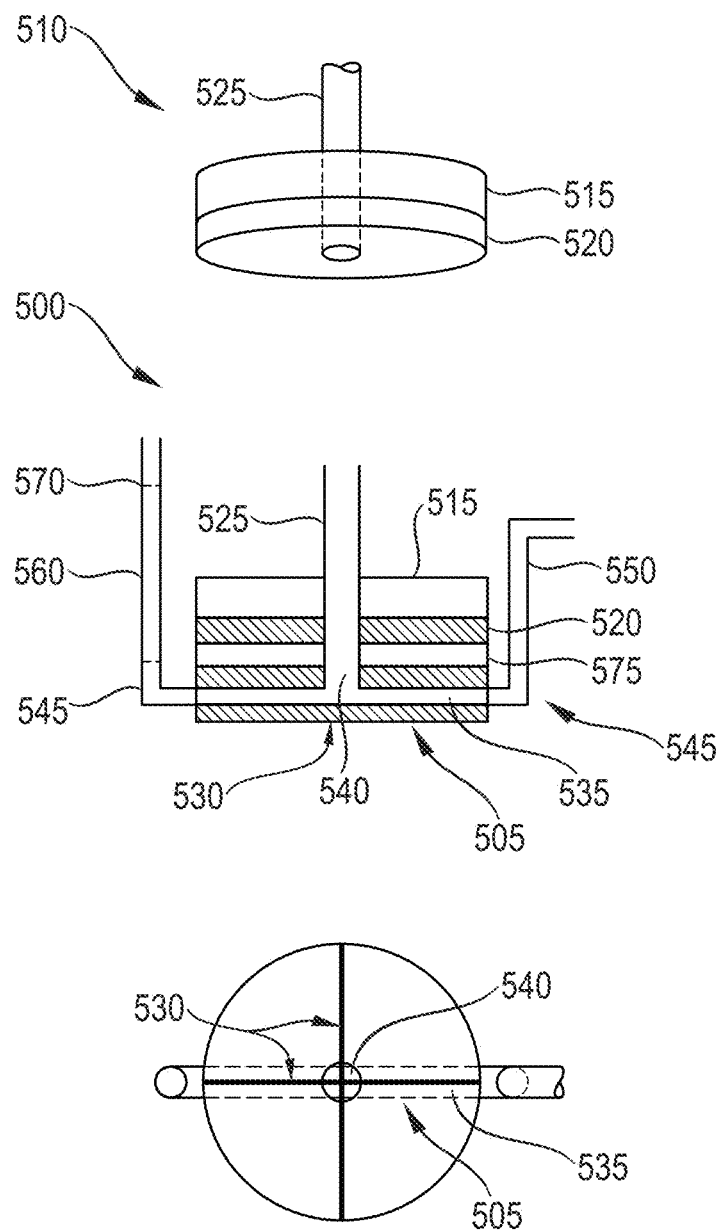
FIGS. 14 and 15 show equipment assemblies used in the In Plane Radial Permeability (IPRP) test for non-swelling Samples.

The IPRP sample holder 500 is shown in FIG. 14 and comprises a cylindrical bottom plate 505, top plate 510, and cylindrical stainless steel weight 515.

Top plate 510 comprises an annular base plate 520, 10 mm thick with an outer diameter of 70.0 mm and a tube 525 of 190 mm length fixed at the center thereof. The tube 525 has in outer diameter of 16 mm and an inner diameter of 12.0 mm. The tube is adhesively fixed into a circular 12 mm hole in the center of the base plate 520 such that the lower edge of the tube is flush with the lower surface of the base plate, as depicted in FIG. 14. The bottom plate 505 and top plate 510 are fabricated from LEXAN® or equivalent. The stainless steel weight 515 has an outer diameter of 70 mm and an inner diameter of 15.9 mm so that the weight is a close sliding fit on tube 525. The thickness of the stainless steel weight 515 is approximately 25 mm and is adjusted so that the total weight of the top plate 510 and the stainless steel weight 515 is 788 g±1 g to provide 2.06 kPa of confining pressure during the measurement.

Bottom plate 505 is approximately 50 mm thick and has two registration grooves 530 cut into the lower surface of the plate such that each groove spans the diameter of the bottom plate and the grooves are perpendicular to each other. Each groove is 1.5 mm wide and 2 mm deep. Bottom plate 505 has a horizontal hole 535 which spans the diameter of the plate. The horizontal hole 535 has a diameter of 11 mm and its central axis is 12 mm below the upper surface of bottom plate 505. Bottom plate 505 also has a central vertical hole 540 which has a diameter of 10 mm and is 8 mm deep. The central hole 540 connects to the horizontal hole 535 to form a T-shaped cavity in the bottom plate 505. The outer portions of the horizontal hole 535 are threaded to accommodate pipe elbows 545 which are attached to the bottom plate 505 in a watertight fashion. One elbow is connected to a vertical transparent tube 560 with a height of 190 mm and an internal diameter of 10 mm. The tube 560 is scribed with a suitable mark 570 at a height of 100 mm above the upper surface of the bottom plate 520. This is the reference for the fluid level to be maintained during the measurement. The other elbow 545 is connected to the fluid delivery reservoir via a flexible tube.

Figure 15:
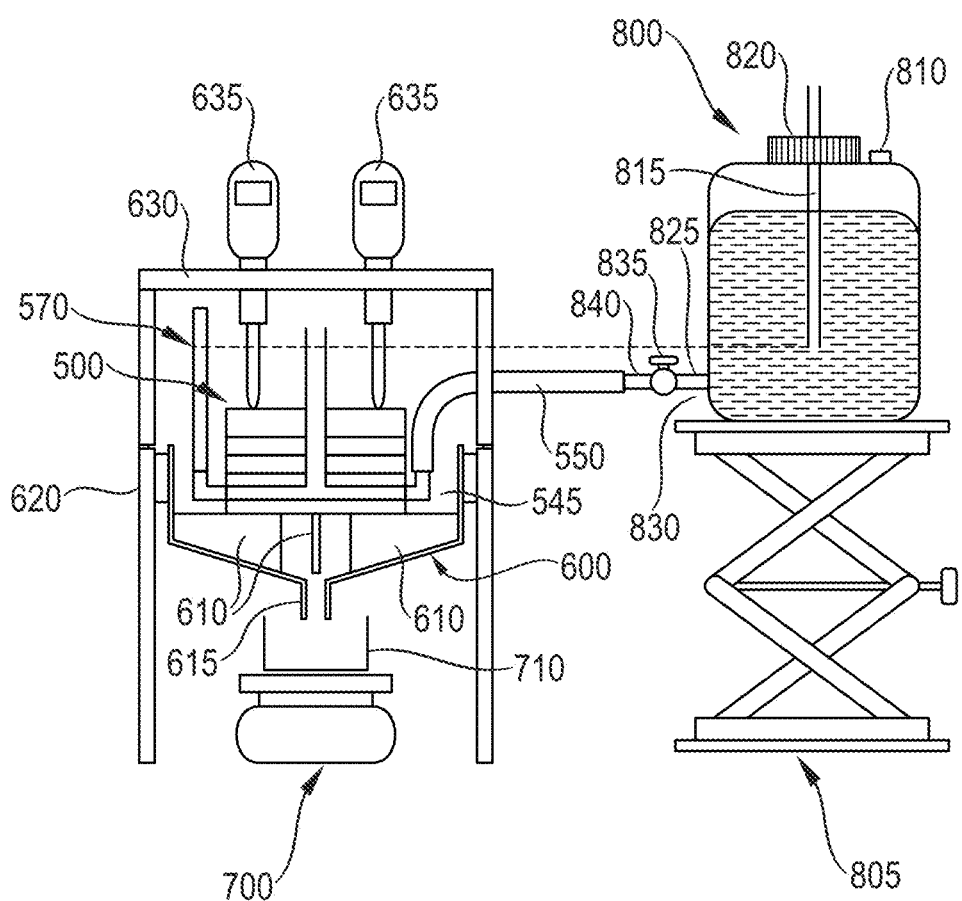

A suitable fluid delivery reservoir 800 is shown in FIG. 15. Reservoir 800 is situated on a suitable laboratory jack 805 and has an air-tight stoppered opening 810 to facilitate filling of the reservoir with fluid. An open-ended glass tube 815 having an inner diameter of 10 mm extends through a port 820 in the top of the reservoir such that there is an airtight seal between the outside of the tube and the reservoir. Reservoir 800 is provided with an L-shaped delivery tube 825 having an inlet 830 that is below the surface of the fluid in the reservoir, a stopcock 835, and an outlet 840. The outlet 840 is connected to elbow 545 via flexible plastic tubing 550 (e.g. TYGON®). The internal diameter of the delivery tube 825, stopcock 835, and flexible plastic tubing 550 enable fluid delivery to the IPRP sample holder 500 at a high enough flow rate to maintain the level of fluid in tube 560 at the scribed mark 570 at all times during the measurement. The reservoir 800 has a capacity of approximately 6 liters, although larger reservoirs may be required depending on the sample thickness and permeability. Other fluid delivery systems may be employed provided that they are able to deliver the fluid to the sample holder 500 and maintain the level of fluid in tube 560 at the scribed mark 570 for the duration of the measurement.

The IPRP catchment funnel 500 is shown in FIG. 14 and comprises an outer housing 605 with an internal diameter at the upper edge of the funnel of approximately 125 mm. Funnel 600 is constructed such that liquid falling into the funnel drains rapidly and freely from spout 615. A stand with horizontal flange 620 around the funnel 600 facilitates mounting the funnel in a horizontal position. Two integral vertical internal ribs 610 span the internal diameter of the funnel and are perpendicular to each other. Each rib 610 is 1.5 mm wide and the top surfaces of the ribs lie in a horizontal plane. The funnel housing 600 and ribs 610 are fabricated from a suitably rigid material such as LEXAN® or equivalent in order to support sample holder 500. To facilitate loading of the sample it is advantageous for the height of the ribs to be sufficient to allow the upper surface of the bottom plate 505 to lie above the funnel flange 620 when the bottom plate 505 is located on ribs 610. A bridge 630 is attached to flange 620 in order to mount two digital calipers 635 to measure the relative height of the stainless steel weight 515. The digital calipers 635 have a resolution of ±0.01 mm over a range of 25 mm. A suitable digital caliper is a Mitutoyo model 575-123 (available from McMaster Carr Co., catalog no. 19975-A73), or equivalent. Each caliper is interfaced with a computer to allow height readings to be recorded periodically and stored electronically on the computer. Bridge 630 has two circular holes 17 mm in diameter to accommodate tubes 525 and 560 without the tubes touching the bridge.

Funnel 600 is mounted over an electronic balance 700, as shown in FIG. 15. The balance has a resolution of ±0.01 g and a capacity of at least 1000 g. The balance 700 is also interfaced with a computer to allow the balance reading to be recorded periodically and stored electronically on the computer. A suitable balance is Mettler-Toledo model PG5002-S or equivalent. A collection container 710 is situated on the balance pan so that liquid draining from the funnel spout 615 falls directly into the container 710.

The funnel 600 is mounted so that the upper surfaces of ribs 610 lie in a horizontal plane. Balance 700 and container 710 are positioned under the funnel 600 so that liquid draining from the funnel spout 615 falls directly into the container 710. The IPRP sample holder 500 is situated centrally in the funnel 600 with the ribs 610 located in grooves 530. The upper surface of the bottom plate 505 must be perfectly flat and level. The top plate 510 is aligned with and rests on the bottom plate 505. The stainless steel weight 515 surrounds the tube 525 and rests on the top plate 510. Tube 525 extends vertically through the central hole in the bridge 630. Both calipers 635 are mounted firmly to the bridge 630 with the foot resting on a point on the upper surface of the stainless steel weight 515. The calipers are set to zero in this state. The reservoir 800 is filled with 0.9% saline solution and re-sealed. The outlet 840 is connected to elbow 545 via flexible plastic tubing 550.

An annular sample 575 of the material to be tested is cut by suitable means. The sample has an outer diameter of 70 mm and an inner hole diameter of 12 mm. One suitable means of cutting the sample is to use a die cutter with sharp concentric blades.

The top plate 510 is lifted enough to insert the sample 575 between the top plate and the bottom plate 505 with the sample centered on the bottom plate and the plates aligned. The stopcock 835 is opened and the level of fluid in tube 560 is set to the scribed mark 570 by adjusting the height of the reservoir 800 using the jack 805 and by adjusting the position of the tube 815 in the reservoir. When the fluid level in the tube 560 is stable at the scribed mark 570 initiate recording data from the balance and calipers by the computer. Balance readings and time elapsed are recorded every 10 seconds for five minutes. The average sample thickness B is calculated from all caliper reading between 60 seconds and 300 seconds and expressed in cm. The flow rate in grams per second is the slope calculated by linear least squares regression fit of the balance reading (dependent variable) at different times (independent variable) considering only the readings between 60 seconds and 300 seconds.

Permeability k (cm$^2$) is then calculated by the following equation:

$$k = \frac{(Q/\rho_l) \cdot \mu \cdot \ln(R_0/R_i)}{2\pi \cdot B \cdot \Delta p}$$

Where:
k is the permeability (cm$^2$).
Q is the flow rate (g/s).
$\rho_l$ is the liquid density (g/cm$^3$).
$\mu$ is the liquid viscosity at 20° C. (Pa*s).
$R_0$ is the outer sample radius (cm).
$R_i$ is the inner sample radius (cm).
B is the average sample thickness (cm).

$\Delta p$ is the pressure drop (Pa) calculated according to the following Equation:

$$\Delta p = \left(\Delta h - \frac{B}{2}\right) \cdot g \cdot \rho_l \cdot 10$$

Where:
$\Delta h$ is the measured liquid hydrostatic pressure (cm).
g is the acceleration constant (m/sec$^2$).
$\rho_l$ is the liquid density (g/cm$^3$).
The permeability k in cm$^2$ is then converted and reported in Darcy as average of 5 replicates rounded to the nearest 0.1 Darcy: 1 Darcy=0.9869×10$^{-12}$ m$^2$.

Fixed Height Saturation (FHS) at 5 cm Test Method

This test is suitable of measuring the saturation of a material at a wicking height of 5 cm providing a measure of the partially saturated suction of such a material once in contact with Saline solution.

Figure 13:
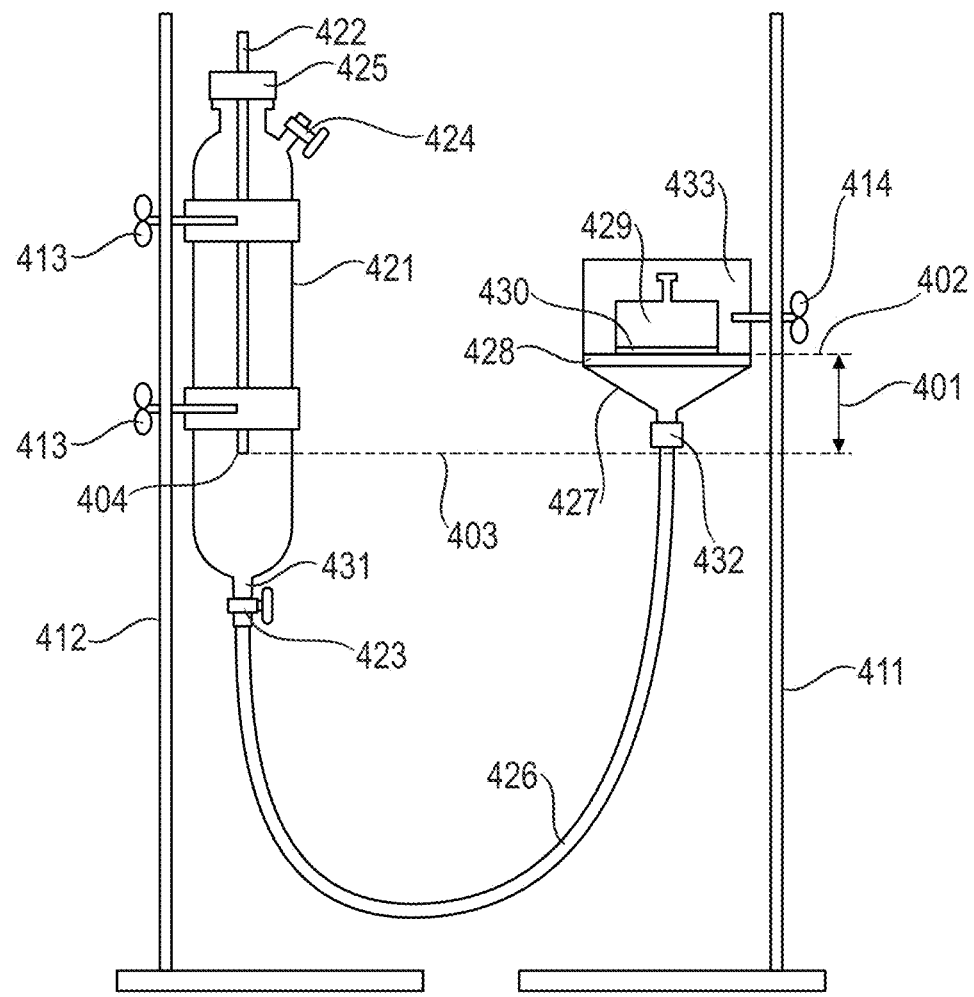
FIG. 13 shows an equipment assembly used in the Fixed Height Saturation (FHS) test.

General Apparatus Setup:

FIG. 13 shows the FHS measurements setup: a suitable fluid delivery reservoir 421, has a an air tight stopcock 424 to allow the air release during the filling of the equipment. An open-ended glass tube 422 having an inner diameter of 10 mm extends through a port 425 in the top of the reservoir such that there is an airtight seal between the outside of the tube and the reservoir, this allows maintaining the required zero level of the hydro head during the experiment regardless the amount of liquid in the reservoir. Reservoir 421 is provided with delivery tube 431 having an inlet at the bottom of the reservoir, a stopcock 423, with the outlet connected to the bottom 432 of the sample holder funnel 427 via flexible plastic tubing 426 (e.g. TYGON®). The Fluid reservoir is firmly held in position by means of standard lab clamps 413 and a suitable lab support 412. The internal diameter of the delivery tube 431, stopcock 423, and flexible plastic tubing 426 enables fluid delivery to the sample holder funnel 427 at a high enough flow rate to completely wet the material in less than 30 seconds. The reservoir 421 has a capacity of approximately 1 liter. Other fluid delivery systems may be employed provided that they are able to deliver the fluid to the sample holder funnel 427 maintaining the zero level of the hydrostatic liquid pressure 403 at a constant height during the whole experiment.

The sample holder funnel 427 has a bottom connector with an internal diameter of 10 mm, a measurement and a chamber 433 where a glass frit 428 is accommodated. The sample holder chamber has a suitable size to accommodate the sample 430 and the confining pressure weight 429. The frit is sealed to the wall of the chamber 433. The glass frit has pore of specific size of 16-40 μm (glass frit type P 40, as defined by ISO 4793) and a thickness of 7 mm.

The confining pressure weight 429 is a cylinder with a diameter identical to the sample size (6 cm) and a weight of 593.94 g so to apply exactly 2.06 kPa of confining pressure to the sample 430. The sample holder funnel 427 is precisely held in position using a suitable lab support 411 through a standard lab clamp 414. The clamp should allow an easy vertical positioning of the sample holder funnel 427 such that the top of the glass frit 428 can be positioned at a) the same height (±1 mm) of the bottom end 404 of the open ended glass tube 422 and b) exactly 5 cm (±1 mm) above the bottom end 404 of the open ended glass tube 422. Alternatively two separated clamps are positioned at the abovementioned setups a and b and the sample holder funnel is alternatively moved from one to the other. During the non usage time, the instrument is kept in proper operating conditions flooding the sample holder funnel 427 with an excess of liquid to guarantee a proper wetting of the glass frit 428 that should be completely below the liquid level. The sample holder funnel 427 is also covered with an air tight cap (not shown) to avoid evaporation and therefore a change in solution salinity. During storage stopcocks 423 and 424 are also accordingly closed to avoid evaporation as well as the open ended tube 422 air tight sealed with a cap (not shown).

Sample Preparation

A disc of 6 cm diameter is prepared according to the above general procedure, the sample should be prepared out of the whole distribution material (e.g. a plurality of wet laid layers or folds).

Material used:

Saline solution at a concentration of 0.9% by weight
FHS equipment
Bubble level
analytical balance with a resolution of ±0.001 g with air draft protections.
Funnel
Tweezers
Timer Experiment Setup Before Starting the Experiment:

1) the caps to the open ended tube 422 and the sample holder funnel 427 are removed.
2) Ensuring the stopcock 423 is closed, the stopcock 424 is opened to allow the air to flow out of the liquid reservoir as displaced by liquid during the refilling phase. The liquid reservoir 421 is refiled through top end of the open-end tube 422 with the 0.9% Saline solution with the help of suitable means such a funnel (not shown) at the end of the filling the stopcock 424 is closed.

If during all the experiments the liquid level would be close to the bottom 404 of the open-ended tube 422, before running the next sample, the liquid reservoir must be refilled repeating this step number 2.

3) The sample holder funnel 427 is removed from the lab clamp 414 and the excess of liquid is removed pouring it away.
4) Manually holding the sample holder funnel 427 such that the top of the glass frit 428 lies around 10 cm below the bottom end 404 of the open-ended tube 422 the stop cock 423 is carefully open until the air liquid interface in the open ended tube 422 reaches the bottom end 404 and a few bubble of air escape from tube 422. At this point the stop cock 423 is closed.
5) The excess of liquid now present in the sample holder funnel 427 is again disposed and the system is now ready to start the measurements.

For each replicate:

1) The sample holder is positioned on the clamp 414 such that the top of the glass frit 428 lies exactly 5 cm (±1 mm) above the bottom end 404 of the open-ended tube 422. To ensure a reliable measure it is checked that the glass frit 428 is perfectly horizontal with the help of a bubble level.
2) Any remaining droplets of liquid on top of the glass frit are carefully removed by means of a filter paper of any other suitable material.
3) The sample is weighed with an analytical balance with a resolution of ±0.001 g. The Weight is recorded as Dry Sample Weight ($W_D$) to the nearest 0.001 g when the readings on the balance become constant.
4) The sample 430 is positioned in the center of the sample holder with the help of tweezers with particular care in not altering the orientation and relative position of each of the layers of the acquisition system. It is important that the topsheet facing side of each layer is facing now downwards during the experiment in the direction of the glass frit 428, reproducing the liquid flow entrance direction correctly.
5) The confining weight 429 is positioned centered on the sample
6) The stopcock 423 is opened for 30±1 seconds allowing liquid to flow in the sample and then closed again.
7) The confining weight 429 and the sample 430 are carefully removed from the glass frit 428 with the help of tweezers, it is important to keep track of the orientation of the sample and the relative position of the layers during the subsequent phases.
8) The sample 430 is weighed with the analytical balance with a resolution of ±0.001 g. The Weight is recorded as 5 cm Sample Weight ($W_5$) to the nearest 0.001 g when the readings on the balance become constant.
9) The sample 430 is positioned back on the frit with the confining weight 429 centered on top and the correct orientation and relative position of the layers.
10) The clamp 414 is moved (or the sample holder funnel 427 is positioned in another clamp) such that the top of the glass frit 428 lies exactly at the same height (±1 mm) of the bottom end 404 of the open-ended tube 422. To ensure a reliable measure it is checked that the glass frit 428 is perfectly horizontal with the help of a bubble level.
11) The stopcock 423 is opened again for 30±1 seconds allowing liquid to flow in the sample and then closed again.
12) The confining weight 429 and the sample 430 are carefully removed from the glass frit 428 with the help of tweezers
13) The sample 430 is weighted with the analytical balance with a resolution of ±0.001 g. The Weight is recorded as 0 cm Sample Weight ($W_0$) to the nearest 0.001 g when the readings on the balance become constant.

The measurements of a sample are now completed and a subsequent replicate can be measured repeating the above steps. Once terminated the series of experiment around 1 cm of liquid is added on the Sample Holder funnel 427 to completely submerge the glass frit 428. All the stopcocks are closed and the cap positioned according to the storage condition explained above to avoid evaporation and ensure reliability of the subsequent measurements.

Calculations:

The FHS at 5 cm ($FHS_5$) is defined according to the following formula, $$FHS_5 = \frac{W_5 - W_D}{W_0 - W_D} \cdot 100$$

$FHS_5$ is rounded to the nearest 0.1 and expressed as percentage.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for personal hygiene, comprising
a liquid permeable topsheet,
a liquid impermeable backsheet,
an absorbent core between the topsheet and the backsheet, the absorbent core comprising an absorbent material,
a distribution material between the topsheet and the absorbent core, wherein the distribution material is notionally divided into a front region, a back region, and a middle region located between the front region and the back region, wherein each of the front, back, and middle regions is about ⅓ of a length of the distribution material,
wherein at least one of the front, back, and middle regions of the distribution material comprises two or more layers,
wherein the two or more layers of the distribution material comprises a fibrous structure comprising wet-laid fibers, wherein the two or more layers of the distribution material exhibit a Wet Burst Strength from about 50 g to about 500 g, according to a Wet Burst Strength Test Method,
wherein at least one of the two or more layers of the distribution material have a dry caliper at a pressure of 2.06 kPa from about 0.1 mm to about 1.0 mm and the two or more layers of the distribution material have a total dry caliper at a pressure of 2.06 kPa from about 1.0 mm to about 30.0 mm, according to a Dry Caliper measurement Test Method,
wherein a portion of the distribution material comprises a sheet of the fibrous structure of the distribution material which is notionally divided into a first portion, a second portion and a third portion, wherein the first portion of the sheet of the fibrous structure is folded onto the second portion, wherein the third portion of the sheet of the fibrous structure is folded onto the folded first portion to form a trifolded sheet of the fibrous structure, and wherein each of the first portion, the second portion, and the third portion form one of the layers of the distribution material.

2. The absorbent article of claim 1 wherein each layer of the two or more layers of the distribution material exhibits a basis weight from 10 to 200 gsm.

3. The absorbent article of claim 1 wherein, at least in the middle region of the distribution material, the distribution material comprises from 2 to 10 layers, and wherein the middle region of the distribution material has an overall basis weight from about 50 gsm to about 250 gsm.

4. The absorbent article of claim 3 wherein further to the middle region, the front and/or back region or a portion of the front and/or back region of the distribution material comprises from 2 to 10 layers, and the front and/or back region of the distribution material has an overall basis weight from about 50 gsm to about 250 gsm and a total dry caliper at a pressure of 2.06 kPa from about 1.0 mm to about 30.0 mm, according to a Dry Caliper measurement Test Method.

5. The absorbent article of claim 1 wherein the two or more layers of the distribution material do not comprise air-laid fibers.

6. The absorbent article of claim 1 wherein the two or more layers of the distribution material comprises a pattern of raised elements.

7. The absorbent article of claim 6 wherein the raised elements of the pattern of raised elements protrude from the two or more layers of the distribution material towards the topsheet and/or the raised elements of the pattern of raised elements protrude from the two or more layers of the distribution material towards the absorbent core.

8. The absorbent article of claim 1 wherein the absorbent material comprises from about 80% to about 100% of superabsorbent polymers by total weight of the absorbent material.

9. The absorbent article of claim 1 wherein the distribution material has a permeability of at least about 150 Darcy, according to an In Plane Radial Permeability Test Method and a Fixed Height Saturation at about 5 cm above about 40%, according to the Fixed Height Saturation Test Method.

10. The absorbent article of claim 1 wherein the two or more layers of the distribution material have a ratio of wet/dry caliper at 2.06 kPa of at least about 0.5.

11. The absorbent article of claim 1 wherein the two or more layers of the distribution material have a ratio of dry caliper at 4.82 kPa/2.06 kPa of at least about 0.5.

12. The absorbent article of claim 1 wherein the portion of the distribution material comprises at least one sheet of the fibrous structure which is C or S-folded to form at least some of the respective two or more layers.

13. The absorbent article of claim 1 wherein a top portion of the distribution material is attached to the topsheet or to any layer between the topsheet and the distribution material by a first pattern of adhesive, and wherein a bottom portion of the distribution material is attached to a substrate of the absorbent core facing the topsheet or to any layer between the substrate of the absorbent core facing the topsheet and the distribution material by a second pattern of adhesive.

14. The absorbent article of claim 1 wherein each layer of the distribution material is attached to each adjacent layer by a pattern of adhesive.

15. The absorbent article of claim 1 wherein the wet-laid fibers of the fibrous structure comprise one or more cationic wet strength resins selected from the group consisting of a base activated epoxide polyamide epichlorohydrin resin, an urea-formaldehyde resin, a melamine formaldehyde resin, a polyamide-epichlorohydrin resin, a polyethyleneimine resin, a polyacrylamide resin, a dialdehyde starch and mixtures thereof.

16. The absorbent article of claim 1 wherein the distribution material comprises longitudinal side edges and wherein said longitudinal side edges are incrementally stretched, slitted or cut.

17. The absorbent article of claim 1 wherein a portion of the distribution material is printed and/or embossed.

18. An absorbent article for personal hygiene comprising
a liquid permeable topsheet,
a liquid impermeable backsheet,
an absorbent core between the topsheet and the backsheet, the absorbent core comprising an absorbent material,
a distribution material between the topsheet and the absorbent core, wherein the distribution material is notionally divided in a front region, a back region, and a middle region located between the front and the back region, wherein each of the front region, the back region, and the middle region is about ⅓ of a length of the distribution material, and wherein at least one of the front, back, and middle regions of the distribution material comprises two or more layers,
wherein the two or more layers of the distribution material comprises a fibrous structure made of wet-laid fibers, wherein the two or more layers of the distribution material exhibit a Wet Burst Strength from about 50 g to about 500 g, according to a Wet Burst Strength Test Method,
wherein at least one of the two or more layers of the distribution material have a dry caliper at a pressure of 2.06 kPa from about 0.1 mm to about 1.0 mm and the two or more layers of the distribution material have a total dry caliper at a pressure of 2.06 kPa from about 1.0 mm to about 30 0 mm, according to a Dry Caliper measurement Test Method,
wherein a portion of the distribution material is formed by folding the portion of the distribution material over itself, and
wherein the portion of the distribution material comprises a sheet of the fibrous structure of the distribution material which is notionally divided into a first portion, a second portion, and a third portion, wherein the first portion of the sheet of the fibrous structure is folded onto the second portion, wherein the third portion of the sheet of the fibrous structure is folded onto the folded first portion to form a trifolded sheet of the fibrous structure, and wherein each of the first portion, the second portion, and third portion form one of the layers of the distribution material.

19. An absorbent article for personal hygiene comprising
a liquid permeable topsheet,
a liquid impermeable backsheet,
an absorbent core between the topsheet and the backsheet, the absorbent core comprising an absorbent material,
a distribution material between the topsheet and the absorbent core, wherein the distribution material is notionally divided in a front region, a back region, and a middle region located between the front and the back region, wherein each of the front region, the back region, and the middle region is about ⅓ of a length of the distribution material, and wherein at least one of the front, back, and middle regions of the distribution material comprises two or more layers,
wherein the two or more layers of the distribution material comprises a fibrous structure made of wet-laid fibers, wherein the two or more layers of the distribution material exhibit a Wet Burst Strength from about 50 g to about 500 g, according to a Wet Burst Strength Test Method,
wherein at least one of the two or more layers of the distribution material have a dry caliper at a pressure of 2.06 kPa from about 0.1 mm to about 1.0 mm and the two or more layers of the distribution material have a total dry caliper at a pressure of 2.06 kPa from about 1.0 mm to about 30 0 mm, according to a Dry Caliper measurement Test Method,
wherein a portion of the distribution material is formed by folding the portion of the distribution material over itself,
wherein the portion of the distribution material comprises at least one sheet of the fibrous structure which is C or S-folded to form at least some of the two or more layers, and
wherein the portion of the distribution material comprises a sheet of the fibrous structure of the distribution material which is notionally divided into a first portion, a second portion, and a third portion, wherein the first portion of the sheet of the fibrous structure is folded onto the second portion, wherein the third portion of the sheet of the fibrous structure is folded onto the folded first portion to form a trifolded sheet of the fibrous structure, and wherein each of the first portion, the second portion, and third portion form one of the layers of the distribution material.

* * * * *